(12) United States Patent
Kamiyama et al.

(10) Patent No.: US 8,105,240 B2
(45) Date of Patent: Jan. 31, 2012

(54) ULTRASONIC IMAGING APPARATUS AND LOW ATTENUATION MEDIUM WITH A PRESCRIBED PATTERN FOR APPARATUS LOCALIZATION

(75) Inventors: Naohisa Kamiyama, Otawara (JP); Yoko Okamura, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 959 days.

(21) Appl. No.: 11/680,174

(22) Filed: Feb. 28, 2007

(65) Prior Publication Data

US 2007/0239006 A1    Oct. 11, 2007

(30) Foreign Application Priority Data

Mar. 10, 2006    (JP) .................. 2006-066710

(51) Int. Cl.
*A61B 8/00* (2006.01)

(52) U.S. Cl. ........ 600/463; 600/459; 600/443; 600/424; 600/437

(58) Field of Classification Search .......... 600/425–427, 600/437–472
See application file for complete search history.

(56) References Cited

U.S. PATENT DOCUMENTS

| | | | | | |
|---|---|---|---|---|---|
| 5,260,985 | A | * | 11/1993 | Mosby | 378/164 |
| 6,117,080 | A | * | 9/2000 | Schwartz | 600/443 |
| 6,554,771 | B1 | * | 4/2003 | Buil et al. | 600/459 |
| 6,675,040 | B1 | * | 1/2004 | Cosman | 600/427 |
| 7,150,716 | B2 | * | 12/2006 | Jones et al. | 600/446 |
| 7,733,329 | B2 | * | 6/2010 | Xie | 345/166 |
| 2007/0276229 | A1 | * | 11/2007 | Adler | 600/426 |

FOREIGN PATENT DOCUMENTS

| JP | 3-32652 | 2/1991 |
|---|---|---|
| JP | 4-4896 | 1/1992 |
| JP | 3272792 | 1/2002 |
| JP | 3288138 | 3/2002 |
| JP | 2002-512835 | 5/2002 |

* cited by examiner

*Primary Examiner* — Brian Casler
*Assistant Examiner* — Rajeev Siripurapu
(74) *Attorney, Agent, or Firm* — Oblon, Spivak, McClelland, Maier & Neustadt, L.L.P.

(57) ABSTRACT

The ultrasonic imaging apparatus comprises an ultrasonic probe, a detecting part, a position analyzing part, a display control part, a display part, and a storage part. The detecting part is mounted on the ultrasonic probe operable to detect a part of a prescribed pattern formed on an ultrasonic low attenuation medium. In the storage part, the prescribed pattern formed on the ultrasonic low attenuation medium has been preliminarily stored. Upon receipt of detection results from the detecting part, the position analyzing part specifies the position of a part of the detected pattern on the prescribed pattern by referring to the prescribed pattern stored in the storage part. The display control part controls the display part to display the positional relation between the ultrasonic probe and the subject to be examined regarding the position of a part of the prescribed pattern that has been detected as the position of the ultrasonic probe.

25 Claims, 14 Drawing Sheets

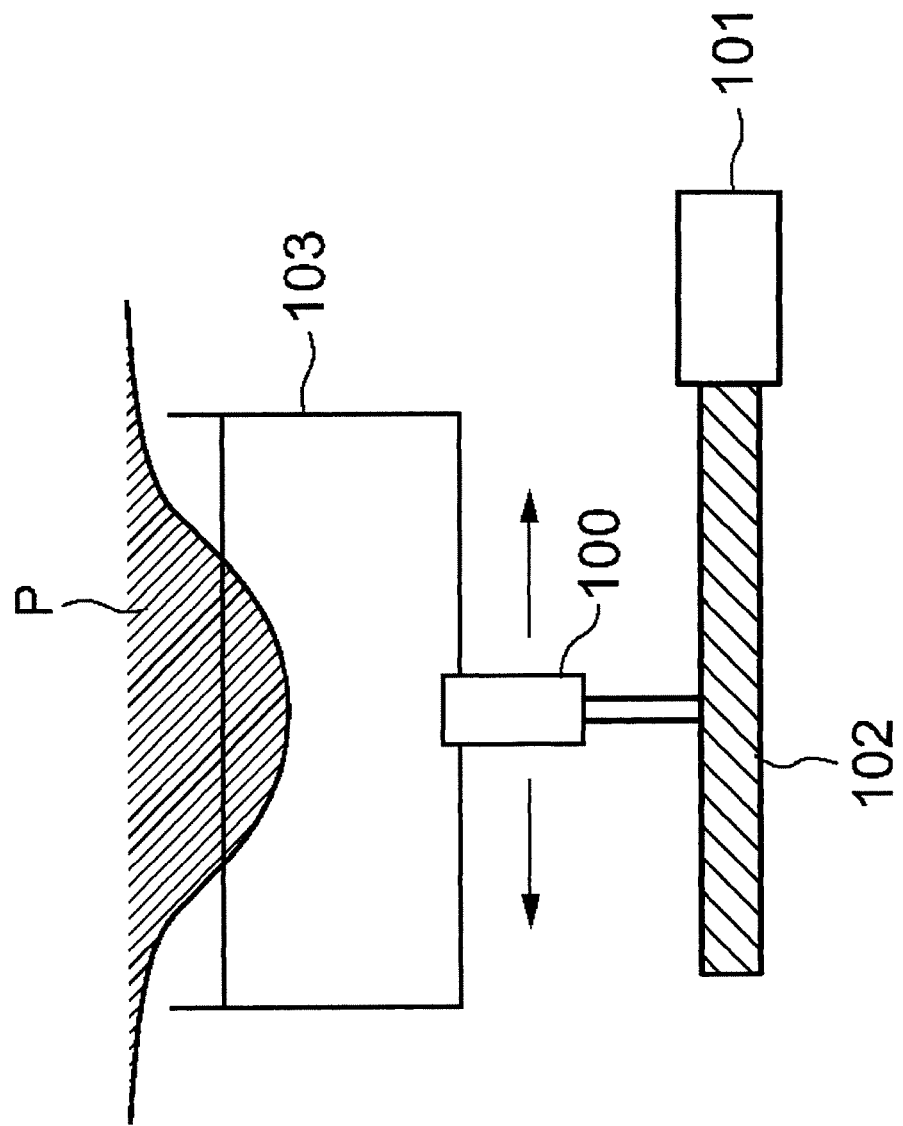

SCANNING DIRECTION
(ARRANGED DIRECTION) X

SCANNING DIRECTION
(ARRANGED DIRECTION) X

ULTRASONIC IMAGING APPARATUS AND LOW ATTENUATION MEDIUM WITH A PRESCRIBED PATTERN FOR APPARATUS LOCALIZATION

BACKGROUND OF THE INVENTION

1. Field of the Invention

The present invention relates to an ultrasonic imaging apparatus as well as an ultrasonic low attenuation medium, and in particular, to a technology for obtaining the scanned position when an image is obtained by scanning a subject to be examined using ultrasonic waves.

2. Description of the Related Art

The ultrasonic imaging apparatus is capable of obtaining images expressing heartbeats or movements of a fetus in real time by a simple operation of applying an ultrasonic probe on the body surface of a subject to be examined. Further, because of the high degree of safety, the examination may be repeated. Furthermore, compared to other diagnostic apparatuses such as an X-ray diagnostic apparatus, X-ray CT apparatus, MRI apparatus, or the like, the size of the system is small, and therefore, it is convenient to conduct examinations at bedsides. Moreover, ultrasonic diagnosis may be used in obstetrics, home care, and the like, without being influenced by the dosage, unlike X-rays.

Further, the ultrasonic imaging apparatus is also frequently used in the examination of breast cancer as with X-ray mammography. X-ray mammography is excellent in its ability to detect microcalcification; however, the ultrasonic waves are said to be more superior in depicting the soft tissues of a living body. Furthermore, X-ray mammography may cause pain, depending on the subject to be examined, since the breasts are sandwiched by pressurizing plates for imaging; however, ultrasonic diagnosis does not cause pain, and, in this respect, ultrasonic diagnosis is said to be more superior to X-ray mammography.

Additionally, in diagnoses using the ultrasonic imaging apparatus, an acoustic coupler to be disposed between the ultrasonic probe and the body surface of the subject to be examined is used in some cases.

The following may be cited as a reason for using an acoustic coupler. For example, in diagnosing a part such as the thyroid gland or carotid artery, an acoustic coupler is used to give some distance between a diagnostic part existing on the body surface and the surface of the ultrasonic probe. Since it is difficult to converge ultrasonic beams directly below the ultrasonic probe, there is a problem of deteriorating the resolution in the region directly below the ultrasonic probe. Therefore, the body surface of the subject to be examined and the surface of the ultrasonic probe are separated so as to enable convergence of ultrasonic beams on the body surface by arranging an acoustic coupler between the ultrasonic probe and the body surface of the subject to be examined.

Also, an acoustic coupler may be used in an automatic diagnostic system (for example, Published Japanese Translation of a PCT No. 2002-512835, Japanese Examined Patent Publication (Kokoku) No. H04-4896). For instance, when applying an ultrasonic probe to a diagnostic part having a curved surface such as the breasts to automatically scan it, linearly scanning via an acoustic coupler, rather than scanning the diagnostic part by directly applying the ultrasonic probe following the curved surface, provides simplified automatic control and a driving mechanism.

The automatic scanning of an ultrasonic probe is described with reference to FIG. 1. FIG. 1 provides a side-view for describing the automatic scanning of an ultrasonic probe. For example, in using water as an acoustic coupler, the breast P is submerged in a water tank 103 filled with water to transmit/receive ultrasonic waves via the acoustic coupler (water). In this case, a movable stage 102 is connected to an ultrasonic probe 100 and is moved via a motor 101 to linearly move the ultrasonic probe 100. As described, automatic scanning may be easily realized by linearly moving the ultrasonic probe 100 through the water tank 103 filled with water (acoustic coupler).

Further, various contraptions have been made for the material or the manufacturing method of an acoustic coupler in order to prevent deterioration of the image quality attributed to excessive attenuation or multiple reflections of the ultrasonic waves accompanied by the acoustic coupler (for example, U.S. Pat. No. 3,288,138, U.S. Pat. No. 3,272,792, Japanese Unexamined Patent Application Publication (Kokai) No. H03-32652).

Furthermore, the ultrasonic imaging apparatus is provided with a body mark function. A body mark is composed of a simplified figure of the diagnostic part and an ultrasonic probe. Marking the position where a tomographic image has been obtained and recording the same along with the tomographic image makes it easier to capture the diagnostic part at the time of diagnostic reading.

One example of a body mark is shown in FIG. 2A and FIG. 2B. In FIG. 2A, the body mark for a liver is shown, and in FIG. 2B the body mark for a breast is shown. The operator may manually move the probe mark Pr representing the position and the orientation of the ultrasonic probe to a position of choice, and record the ultrasonic image at the obtained position by attaching the probe mark Pr.

In actuality, to image a liver or heart, body marks may not be used. When imaging a liver or heart, since characteristic structures such as the portal vein or gallbladder are depicted in the tomographic image, in many cases the position where the tomographic image has been obtained (scanned position) may be captured even without using body marks. Contrary to this, in the event of imaging breasts, body marks are used. Since the breast is symmetrically shaped having the papilla in the center, just by looking at the tomographic image, it is difficult to capture the position where the tomographic image has been obtained (scanned position). In the US and Europe, standard regulations for body marks, etc. have been proposed at academic conferences and similar forums.

However, the ultrasonic imaging apparatus is not necessarily widely used as a diagnostic apparatus for examining breast cancer. The reason is that the examination using ultrasonic waves relies largely on the skill or experience of the examining technologist. In a general ultrasonic diagnosis, the operator (examining technologist) obtains the tomographic image of the diagnostic part by an ultrasonic probe, and later the diagnostic reading of the tomographic image is conducted by a doctor. It is therefore essential to obtain a tomographic image with sufficient accuracy such that it is capable of undergoing diagnostic reading by the doctor. As for the tomographic image obtained by ultrasonic waves, since the image quality changes depending on the set up, such as the way the ultrasonic probe is applied or the gain setting of the apparatus, etc., the technologist is required to learn the scanning technology to be able to obtain an image quality that is satisfactory to the doctor conducting the diagnostic reading.

Moreover, even if the image quality is good, just a diagnostic reading of the tomographic image is insufficient to determine which region of the breast has been scanned to obtain the image. Further, it is also difficult to determine whether the entire region has been scanned or not. For recording, the body mark may be appended to the tomographic image. However, conventionally, since it is an operator (examining technologist) who determines the position where the tomographic image is obtained (scanned position) and inputs the position on the body mark manually, there is concern of a possible increase in examining hours or input errors. In an actual examination, since imaging of many patients within a short period of time is required, in some cases, the work of inputting the position where the tomographic image has been obtained is omitted, or a wrong position is entered. As described, if the input is omitted or if a wrong position is entered, then it becomes a problem to find out which region has been scanned to obtain the tomographic image.

SUMMARY OF THE INVENTION

The present invention is intended to provide an ultrasonic imaging apparatus capable of easily capturing the scanned position when an image is obtained by scanning a subject to be examined using ultrasonic waves, and an ultrasonic low attenuation medium used in the ultrasonic imaging apparatus.

The first embodiment of the present invention is an ultrasonic imaging apparatus comprising an ultrasonic probe; a detecting part mounted on said ultrasonic probe operable to detect a part of prescribed pattern that has been formed on an ultrasonic low attenuation medium arranged in contact with a subject to be examined, a position analyzing part operable to specify a position of said ultrasonic probe on said ultrasonic low attenuation medium, based on the detection results of said detecting part, and a display control part operable to control a display part to display the positional relation between said ultrasonic probe and said subject to be examined.

According to the first embodiment, a pattern formed on the ultrasonic low attenuation medium that is disposed on a subject to be examined is detected by the detecting part and the position of the ultrasonic probe on the ultrasonic low attenuation medium is specified in order to make it possible to automatically specify the position of the ultrasonic probe. As a result, the position of the ultrasonic probe may be easily captured, and thus, it becomes possible to easily capture the position where the ultrasonic image has been obtained (position scanned by the ultrasonic probe).

Furthermore, the second embodiment is an ultrasonic imaging apparatus comprising an ultrasonic probe; a receiving part disposed at said ultrasonic probe operable to receive unique identifying information transmitted by a plurality of transmitting parts disposed at the ultrasonic low attenuation medium for transmitting the unique identifying information respectively, the ultrasonic low attenuation medium arranged in contact with a subject to be examined; a position analyzing part operable to identify the position of said ultrasonic probe on said ultrasonic low attenuation medium, based on the unique identifying information received by said receiving part; and a display control part operable to control the display part to display the positional relation between said ultrasonic probe and said subject to be examined.

According to the second embodiment, the receiving part receives unique information transmitted from the transmitting part that has been received by the ultrasonic low attenuation medium, and the position of the ultrasonic probe on the ultrasonic low attenuation medium is specified, hence making it possible to automatically specify the position of the ultrasonic probe. As a result, the position of the ultrasonic probe may be easily captured, and thus, it becomes possible to easily capture the position where the ultrasonic image has been obtained (position scanned by the ultrasonic probe).

The third embodiment of the present invention is an ultrasonic low attenuation medium, arranged in contact with a subject to be examined and having a prescribed pattern to be detected by the detecting part mounted on the ultrasonic probe.

BRIEF DESCRIPTION OF THE DRAWINGS

FIG. 1 is a side view of the automatic scanning of an ultrasonic probe related to prior arts.

DETAILED DESCRIPTION OF THE EMBODIMENTS

Embodiment 1

Constitution

Figure 2A:
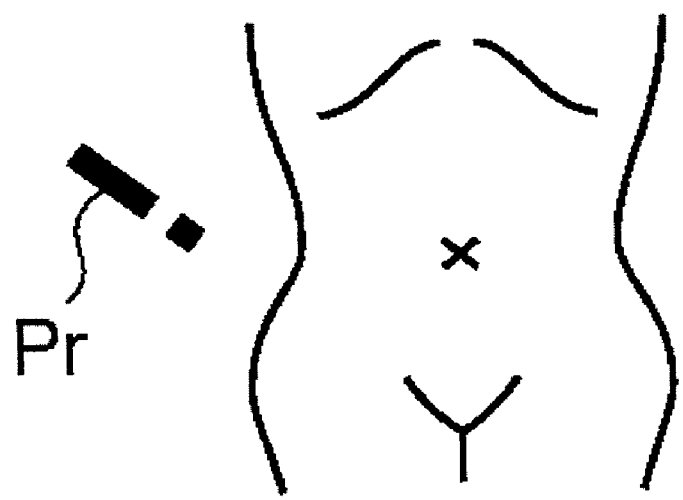
FIG. 2A shows a body mark.
Figure 2B:
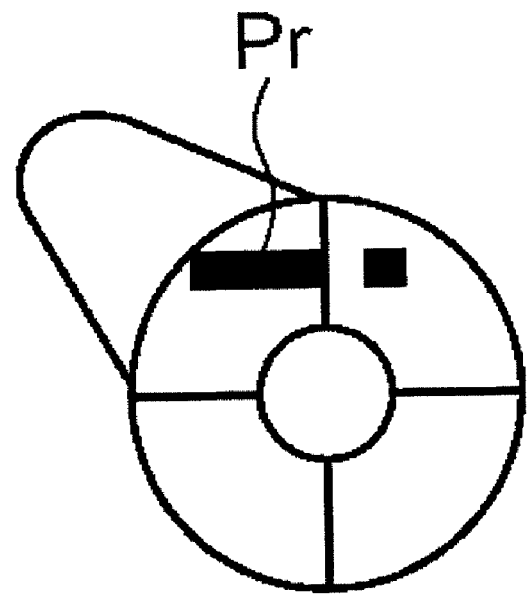
FIG. 2B shows a body mark.
Figure 3:
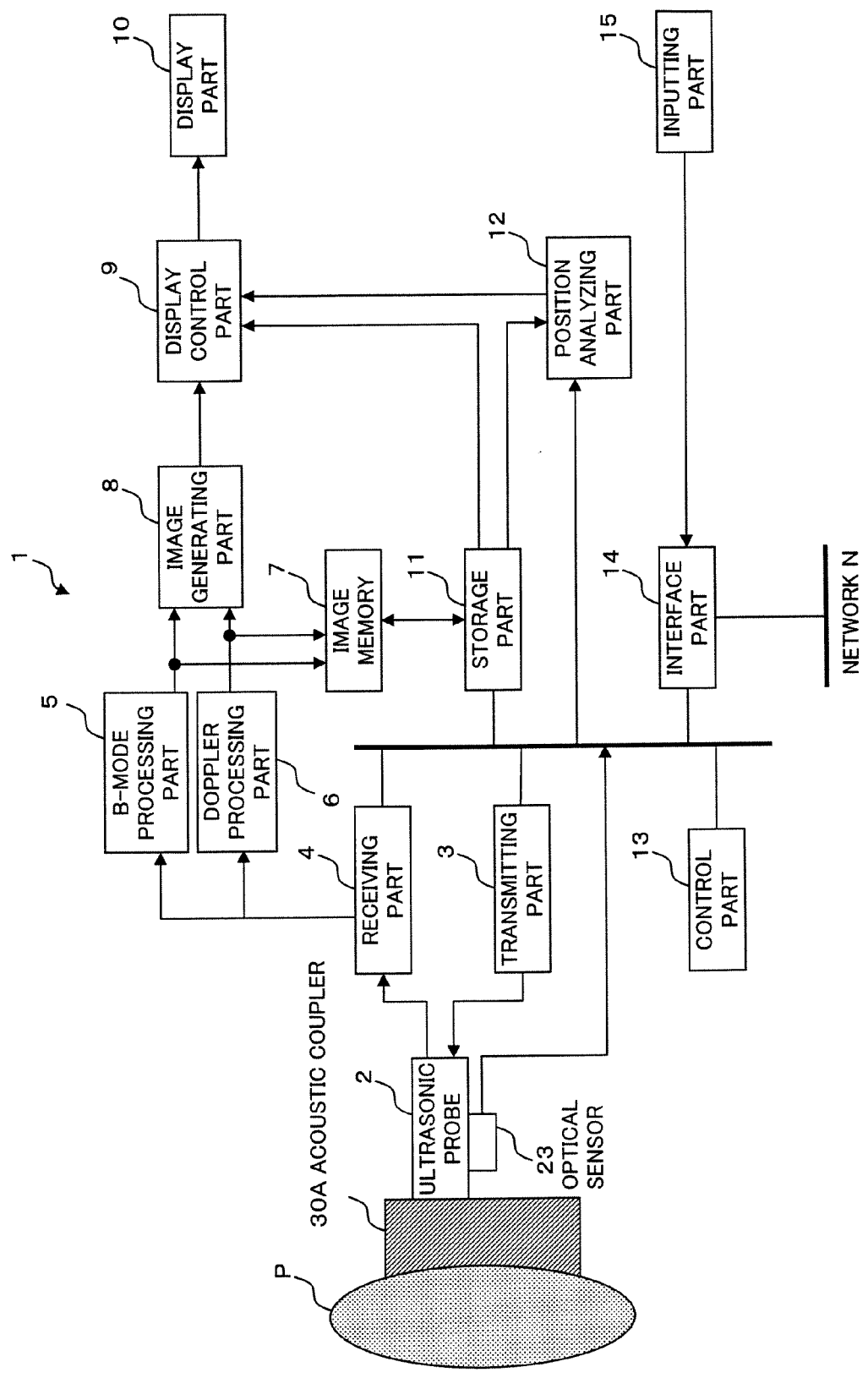
FIG. 3 is a block diagram showing an ultrasonic imaging apparatus related to the first embodiment of the present invention.

The constitution of an ultrasonic imaging apparatus related to the first embodiment of the present invention is described with reference to FIG. 3. FIG. 3 is a block diagram showing the ultrasonic imaging apparatus related to the first embodiment of the present invention.

As for the ultrasonic imaging apparatus related to the first embodiment, an acoustic coupler 30A which is one example of the ultrasonic low attenuation medium are arranged on the body surface of the subject to be examined P, and an ultrasonic probe 2 are arranged on the acoustic coupler 30A, so that ultrasonic waves are transmitted/received via the acoustic coupler 30A. An optical sensor 23 is mounted on the ultrasonic probe 2, and a pattern that the optical sensor 23 is capable of reading is formed on the acoustic coupler 30A. A pattern formed on the acoustic coupler 30A is detected by an optical sensor 21 to obtain the position of the ultrasonic probe 2 on the acoustic coupler 30A, and the positional relation between the subject to be examined P and the ultrasonic probe 2 is displayed on a display part 10. This makes it possible for an operator to easily capture the position of the ultrasonic probe 2 on the acoustic coupler 30A, that is the position where the ultrasonic image has been obtained. Further, the information indicating the positional relation between the subject to be examined P and the ultrasonic probe 2 is stored in a storage part 11, and the information indicating the ultrasonic image and the position are displaying on a display part 10 at the time of diagnostic reading, so that the region where the ultrasonic image has been obtained may be easily captured, thus, making it easier to determine the scanned region where the ultrasonic image has been obtained.

The ultrasonic probe 2 may be a one-dimensional ultrasonic probe with a plurality of ultrasonic transducers arranged in one row in the prescribed direction (scanning direction) or a two-dimensional ultrasonic probe with ultrasonic transducers arranged two-dimensionally.

A transmitting part 3 supplies electrical signals to the ultrasonic probe 2 to generate ultrasonic waves. The transmitting part 3 is provided with a clock generation circuit, a transmission delay circuit and a pulsar circuit (not shown in the figure). The clock generation circuit is a circuit for generating the clock signals to determine the transmission timing or the transmission frequency of the ultrasonic wave signal. The transmission delay circuit applies a delay at the time of transmitting ultrasonic waves to execute transmission focus. The pulsar circuit, housing a pulsar in a number of individual channels corresponding to each ultrasonic transducer, generates a driving pulse at the transmission timing that is delayed to supply to each ultrasonic transducer of the ultrasonic probe 2.

A receiving part 4 receives signals from the ultrasonic probe 2. The receiving part 4 is provided with a preamplifier circuit, an A/D conversion circuit, and a reception delay/adder circuit (not shown in the figure). The preamplifier circuit amplifies the echo signals output from each ultrasonic transducer of the ultrasonic probe 2 for each receiving channel. The A/D conversion circuit provides A/D conversion of the amplified echo signals. The reception delay/adder circuit provides a delay time required to determine the receiving directivity of the echo signals provided with the A/D conversion for adding. By this addition, the reflected component in the direction of the receiving directivity is emphasized.

A B-mode processing part 5 executes band pass filter processing to the signals output from the receiving part 4, and then detects the envelope of the output signals, and applies compression processing on the detected data by means of logarithmic conversion to generate data, and therein, the signal intensity is expressed in the brightness. An image generating part 8 generates B-mode tomographic image data, and therein, the intensity of the reflection wave is expressed in the brightness, based on the data generated by the B-mode processing part 5. The tomographic image based on the B-mode tomographic image data is displayed on the display part 10.

A Doppler processing part 6 obtains blood flow information at various points such as the average speed, dispersion, power, etc., based on the signals output from the receiving part 4. The obtained blood flow information is sent to the image generating part 8 and displayed on the display part 10 as average speed image, dispersion image, power image or a combination of these.

The image generating part 8 reads the processed data, represented by scanning line signal rows output from the B-mode processing part 5 or the Doppler processing part 6 and converts it into data of a coordinate system based on the space information (scan conversion process). That is, in order to be able to display the signal rows synchronized with the ultrasonic scanning on the display part 10 of a television scanning mode, the scanning mode is converted with synchronizing with standard television scanning to read out. The image generating part 8 includes a memory for storing image data so that the recorded image during the examination may be read, for example, after a diagnosis.

An image memory 7 is a memory for saving ultrasonic image data corresponding to a plurality of frames immediately before freezing. It is also possible to display ultrasonic dynamic images such as tomographic images, etc., by continuously displaying (cine image) the images stored in the image memory 7.

A control part 13 controls the entire operation of the ultrasonic imaging apparatus. The control part 13 reads a control program (not shown in the figure) for executing processes, such as generation or display of images stored in the storage part, and execute processes such as calculations or controls related to various processes.

An interface part 14 is an interface used for connection of an input part 15, a network N or a new external storage device (not shown in the figure). Ultrasonic image data or analysis results, etc. may be transferred by the interface part 14 to other devices via the network N.

An inputting part 15 comprises a pointing device such as a joystick or trackball, switches, various buttons, mouse and keyboard or TCS (Touch Command Screen), etc. The operator may use the inputting part 15 to give the apparatus various instructions, set instructions of transmitting/receiving conditions of ultrasonic waves and of ROI (Region Of Interest), or set instructions of image quality conditions, etc.

Next, the constitution and the function of the acoustic coupler, optical sensor 23, position analyzing part 12, and display control part 9 are described.

Acoustic Coupler

Figure 4A:
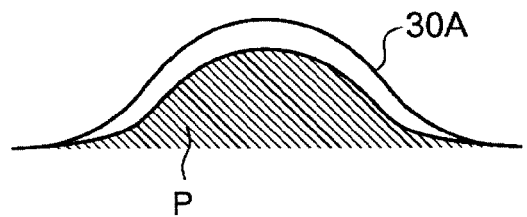
FIG. 4A is a cross-sectional drawing showing an acoustic coupler used in the ultrasonic imaging apparatus related to the first embodiment of the present invention.
Figure 4B:
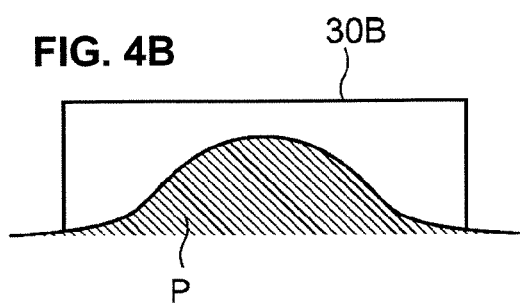
FIG. 4B is a cross-sectional drawing showing an acoustic coupler used in the ultrasonic imaging apparatus related to the first embodiment of the present invention.
Figure 4C:
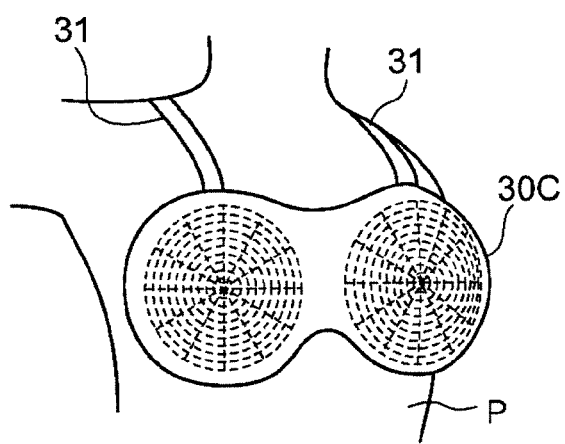
FIG. 4C is an oblique view of an acoustic coupler used in the ultrasonic imaging apparatus related to the first embodiment of the present invention.

First, the shape of the acoustic coupler is described with reference to FIG. 4A, FIG. 4B, and FIG. 4C. FIG. 4A and FIG. 4B are cross-sectional drawings showing an acoustic coupler used in the ultrasonic imaging apparatus related to the first embodiment of the present invention. FIG. 4C is an oblique view of an acoustic coupler used in the ultrasonic imaging apparatus related to the first embodiment of the present invention.

In the first embodiment, three kinds of acoustic couplers 30A, 30B and 30C, shown in FIG. 4A, FIG. 4B and FIG. 4C, are described. The acoustic coupler related to the first embodiment is not limited to these examples. In the first embodiment, acoustic couplers used in diagnosing breasts are further described.

The acoustic couplers 30A, 30B and 30C that are shown in FIG. 4A, FIG. 4B and FIG. 4C are composed of a material that is excellent in adapting to a patient's body and in ultrasonic permeability. It is desirable that the acoustic couplers 30A, 30B and 30C be made from a material that is flexible but having physical strength and good ultrasonic permeability, and is durable in the sterilization process. Specifically, for the acoustic couplers 30A, 30B and 30C, a material with small ultrasonic attenuation is used, and moreover, it is desirable to use a material whose acoustic impedance value is close to the acoustic impedance of the subject to be examined (patient's body).

As for the material of the acoustic couplers 30A, 30B and 30C, for example, nonaqueous gel materials such as urethane rubber, or silicon rubber, and polymeric hydrogels such as polyvinyl alcohol (PVA) or polyethylene oxide (PEO), have been used. Further, in the case of a material that is flexible and difficult to maintain a shape, the shape may be maintained by covering the surface of the acoustic couplers 30A, 30B and 30C with silicon rubber and the like. These acoustic couplers 30A, 30B and 30C are examples of an ultrasonic low attenuation medium.

The acoustic coupler 30A is used closely attached to the subject to be examined (breast) P as shown in the cross-sectional drawing of FIG. 4A. The acoustic coupler 30A has a surface contacting the subject to be examined (breast) P, formed in a concave configuration to match the shape of the breast so as to be closely attached to the subject to be examined P (breast). The acoustic coupler 30A is of a relatively thin type, for example, a brassiere made of silicon, and the acoustic coupler 30A may be closely attached to the subject to be examined (breast) P with an adhesive material for the inside. Moreover, a gel that is normally used in ultrasonic diagnoses may also be applied between the breast and the acoustic coupler 30A. By arranging the ultrasonic probe 2 on the acoustic coupler 30A, ultrasonic waves are transmitted/received via the acoustic coupler 30A.

Another style of acoustic coupler is shown in FIG. 4B. The acoustic coupler 30B shown in FIG. 4B is a relatively thick type, and the surface contacting the subject to be examined (breast) P is formed in a concave configuration to match the shape of the breast so as to be closely attached to the subject to be examined (breast) P. Furthermore, the acoustic coupler 30B has a flatly shaped opposite surface that contacts the subject to be examined (breast) P. By flattening the surface, since the ultrasonic probe 2 may be applied perpendicularly to the acoustic coupler 30B, the scanning of the ultrasonic probe 2 becomes easier. Also, there is merit in making it relatively easier to print patterns to be described later.

Another style of the acoustic coupler is shown in FIG. 4C. For the acoustic coupler 30C shown in FIG. 4C, shoulder straps 31 is provided, and the patient may wear the acoustic coupler 30C by slipping their arms through the shoulder straps 31. As a result, both breasts may be covered by the acoustic coupler 30C. As described, by providing shoulder straps 31 for the acoustic coupler 30C, since the acoustic coupler 30C may be used hanging from the shoulders, the patient may receive an examination in a sitting position. Further, if the acoustic coupler 30C is put on in a changing room, etc., the examination may be done without exposing the breasts; therefore, it becomes possible to relieve the patient's stress. Furthermore, although this acoustic coupler 30C covers both breasts, only one strap can be used to hang from the shoulder.

In the first embodiment, an acoustic coupler used when diagnosing breasts is described. In the case of diagnosing parts other than the breasts, the shape of the acoustic coupler may have to be made to match the shape of the body surface to which the acoustic coupler is closely attached.

Also, as an acoustic coupler, an acoustic coupler in the form of a film (sheet) where the pattern described above has been formed may also be used.

Patterns Formed on the Acoustic Couplers

Patterns detectable by the optical sensor 23 mounted on the ultrasonic probe 2 are formed on the acoustic couplers 30A, 30B and 30C. The patterns are described with reference to FIG. 5A, FIG. 5B, FIG. 5C and FIG. 5D. FIG. 5A, FIG. 5B, FIG. 5C and FIG. 5D are figures showing patterns formed on the acoustic couplers. In the first embodiment, four kinds of patterns are described. The first embodiment is not limited to these patterns. If the pattern is detectable by the optical sensor 23 and the position of which is identifiable, the pattern may be included in the patterns of the present invention.

The patterns formed on the acoustic couplers 30A, 30B and 30C have shapes, letters, or colors, etc., detectable by the optical sensor 23. When the ultrasonic probe 2 scans the subject to be examined (breast) P via acoustic couplers 30A, 30B and 30C, the pattern in a position at which the ultrasonic probe 2 has been arranged is detected by the optical sensor 23 and output to the position analyzing part 12 to be described later, and the position of the ultrasonic probe 2 is specified by the position analyzing part 12.

Figure 5B:
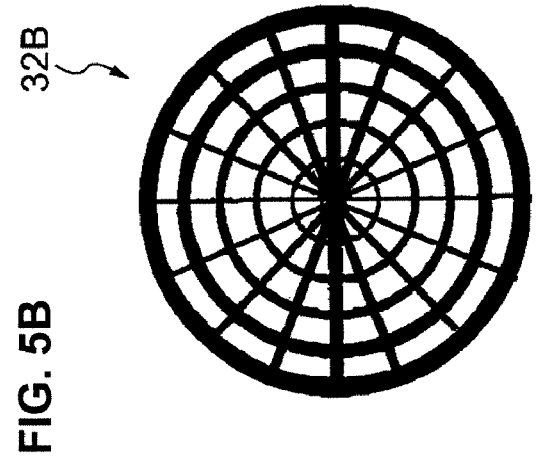
FIG. 5B shows a pattern formed on an acoustic coupler used in the ultrasonic imaging apparatus related to the first embodiment of the present invention.
Figure 5D:
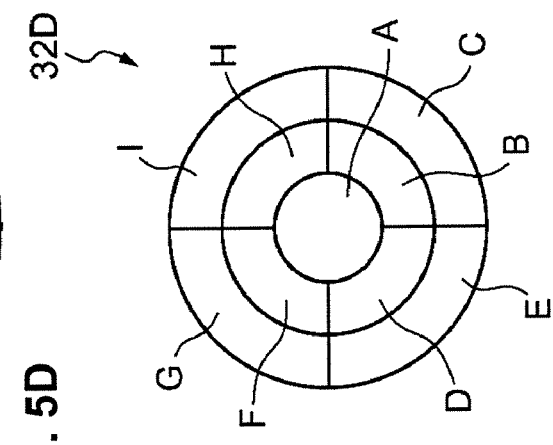
FIG. 5D shows a pattern formed on an acoustic coupler used in the ultrasonic imaging apparatus related to the first embodiment of the present invention.
Figure 5A:
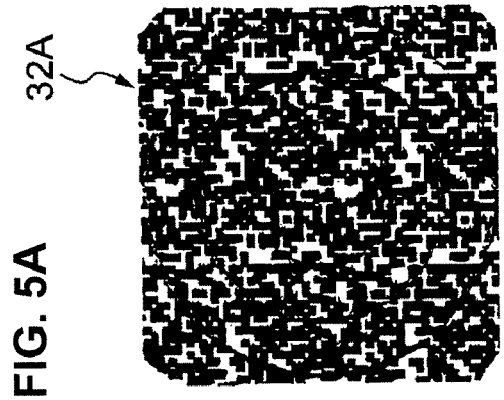
FIG. 5A shows a pattern formed on an acoustic coupler used in the ultrasonic imaging apparatus related to the first embodiment of the present invention.

The pattern 32A shown in FIG. 5A is configured by two-dimensional codes, divided into regions. In detail, the pattern 32A is a block-shaped code pattern comprising white and black squares, and the arrangement of the white and the black squares is different depending on the position (coordinate). As described, since the arrangement of the white and the black squares is different depending on the position (coordinate), the local pattern, detected by the optical sensor 23 and the pattern 32A preliminarily stored in the storage part 11, may be matched to uniquely specify the position of the local pattern on the pattern 32A. From this, it becomes possible to uniquely specify the position of the ultrasonic probe 2 on the acoustic coupler 30A. Moreover, as pattern 32A, with the use of a pattern such as QR code (two-dimensional bar code) used for product labels, etc., the position of a local pattern that has been detected may also be specified.

The pattern 32B shown in FIG. 5B is configured by a plurality of concentric circles and a plurality of straight lines radially stretching from the center of the concentric circles like radiation rays. This plurality of concentric circles and the plurality of straight lines differ in their widths. As described, since the widths of the individual lines differ, the local pattern, detected by the optical sensor 23 and the pattern 32B preliminarily stored in the storage part 11, may be matched to uniquely specify the position of the local pattern on the pattern 32B. As a result, it becomes possible to uniquely specify the position of the ultrasonic probe 2 on the acoustic coupler 30A.

Figure 5C:
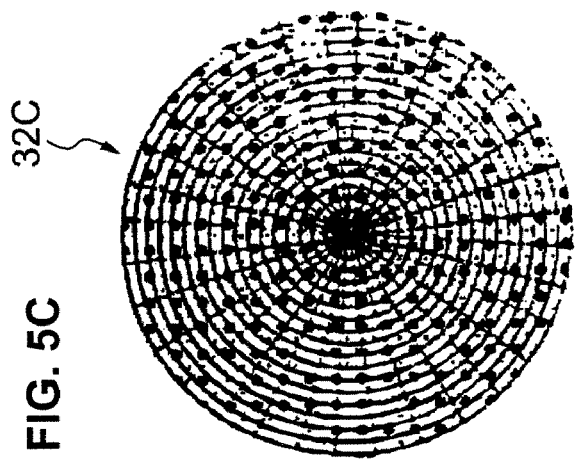
FIG. 5C shows a pattern formed on an acoustic coupler used in the ultrasonic imaging apparatus related to the first embodiment of the present invention.

The pattern 32C shown in FIG. 5C is configured by the combination of a plurality of concentric circles, a plurality of straight lines radially stretching from the center of the concentric circles like radiation rays and a plurality of dots, and the arrangement differs depending on the position. Thereby, the local pattern, detected by the optical sensor 23 and the pattern 32C preliminarily stored in the storage part 11, may be matched to uniquely specify the position of the local pattern on the pattern 32C. As a result, it becomes possible to uniquely specify the position of the ultrasonic probe 2 on the acoustic coupler 30A.

The pattern 32D shown in FIG. 5D is configured by a plurality of regions, and the individual region is tinted with different colors, respectively. For example, the pattern 32D comprises the regions A to I, and each region from A to I is tinted with different colors, respectively. By changing the combination of the colors or the shape of the region, the local pattern, detected by the optical sensor 23 and the pattern 32D preliminarily stored in the storage part 11, may be matched to uniquely specify the position of the local pattern on the pattern 32D. As a result, it becomes possible to uniquely specify the position of the ultrasonic probe 2 on the acoustic coupler 30A.

The pattern 32D shown in FIG. 5D has a relatively small number of divided regions. Although it depends on the purpose or kind of diagnosis, even such an approximate capturing of the position may sometimes be sufficient for diagnosis. Also, by using many colors and increasing the number of divisions of the pattern 32D, the position may be specified in detail. Moreover, by using a gradation pattern with gradually changing colors, more detailed information of the oriented position information may be obtained and the position of the ultrasonic probe 2 may be specified in detail.

The above patterns 32A, 32B, 32C and 32D may be formed on the surface of the acoustic couplers 30A, 30B and 30C, or they may also be formed internally.

The data showing the above patterns 32A, 32B, 32C and 32D is preliminarily stored in the storage part 11. Further, in the storage part 11, body mark data comprising schematic figures of diagnostic parts and probe mark data to be displayed on the body mark on the display part 10 are stored. Moreover, in the storage part 11, transmitting/receiving conditions of ultrasonic waves, the control program for executing the image generation and the display process, diagnostic information such as patient's ID, or opinions of doctors, etc., the diagnostic protocol and the like are stored. The storage part 11 may also be used for archiving images that have been stored in the image memory 7.

Optical Sensor

Figure 6:
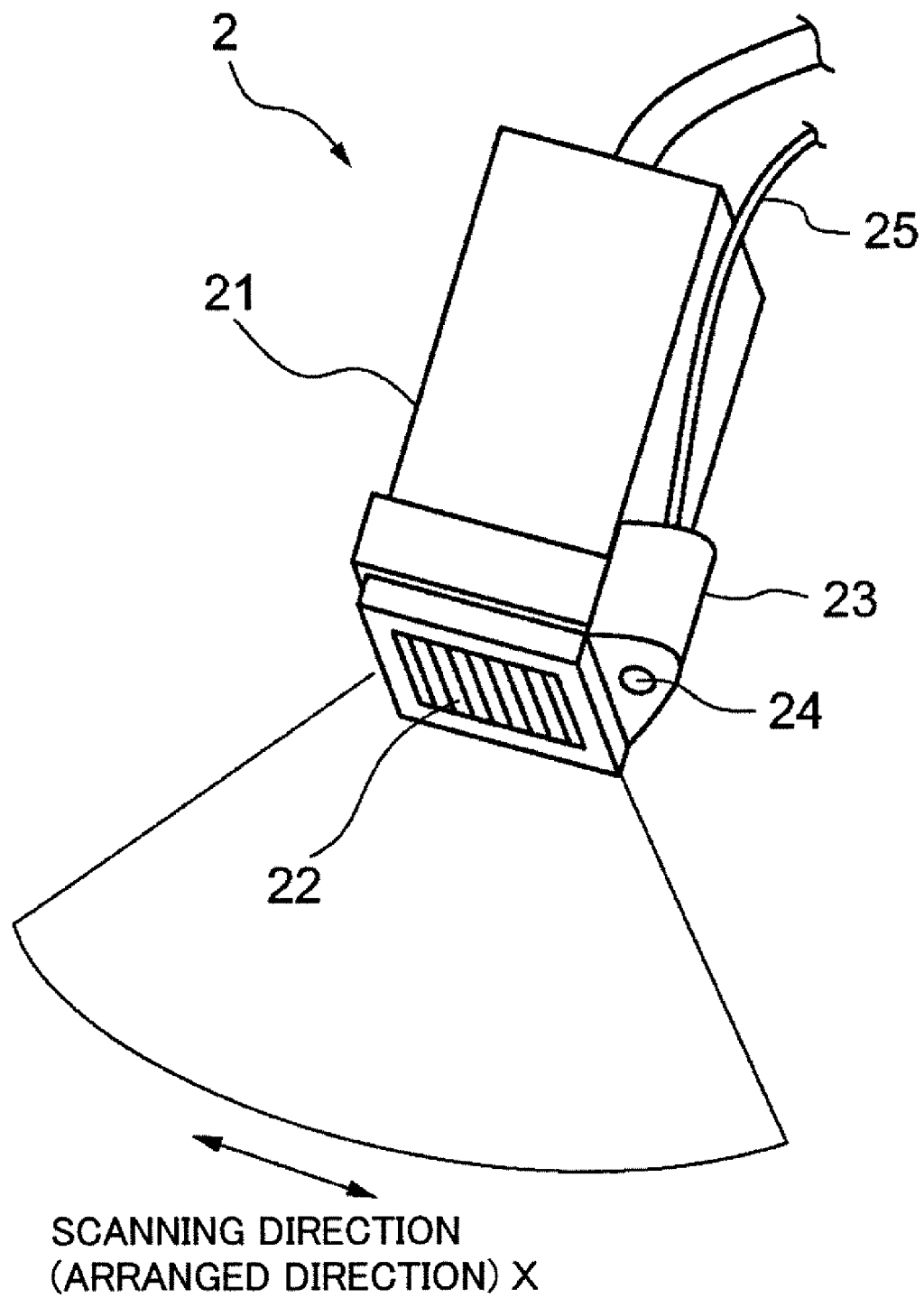
FIG. 6 is an oblique view of an ultrasonic probe and an optical sensor used in the ultrasonic imaging apparatus related to the first embodiment of the present invention.
Figure 7A:
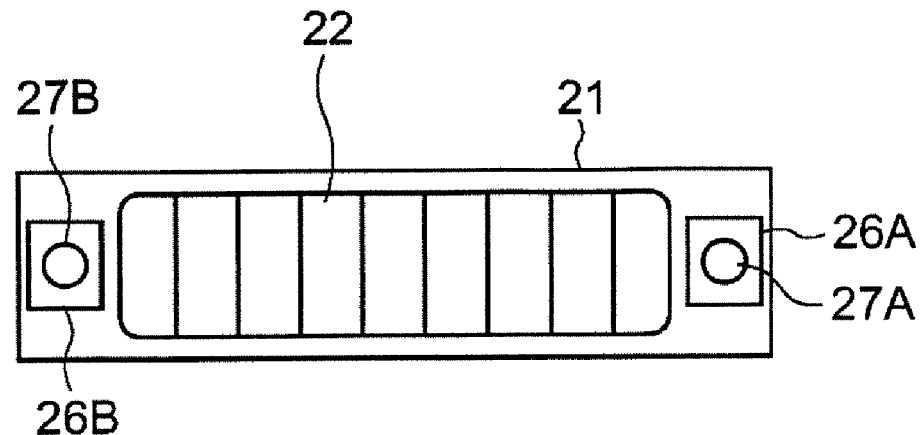
FIG. 7A is a plane drawing showing another ultrasonic probe and optical sensors used in the ultrasonic imaging apparatus related to the first embodiment of the present invention.
Figure 7B:
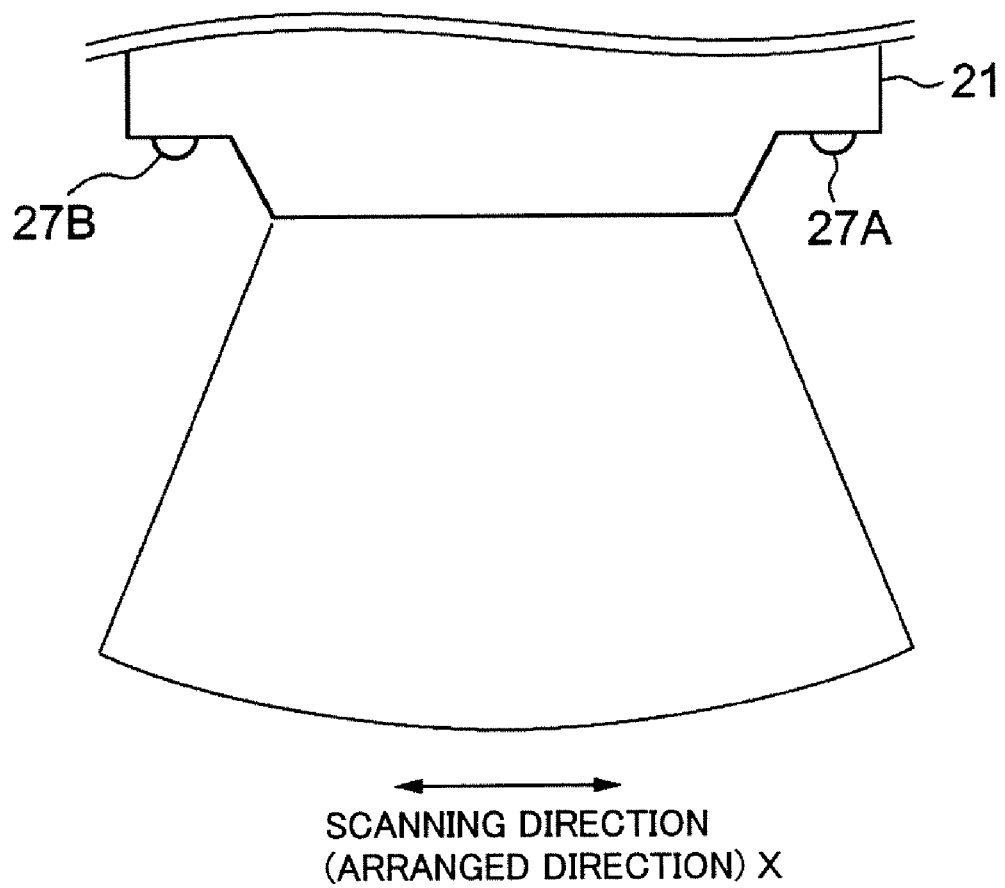
FIG. 7B is a front view of another ultrasonic probe and optical sensors used in the ultrasonic imaging apparatus related to the first embodiment of the present invention.

Next, the optical sensor 23 mounted on the ultrasonic probe 2 is described with reference to FIG. 6, FIG. 7A and FIG. 7B. FIG. 6 is an oblique view of an ultrasonic probe and an optical sensor used in the ultrasonic imaging apparatus related to the first embodiment of the present invention. Further, FIG. 7A is a plane drawing showing another ultrasonic probe and optical sensors used in the ultrasonic imaging apparatus related to the first embodiment of the present invention. Furthermore, FIG. 7B is a front view of another ultrasonic probe and optical sensors used in the ultrasonic imaging apparatus related to the first embodiment of the present invention.

As shown in FIG. 6, the optical sensor 23 is mounted on the side surface of a case 21 of the ultrasonic probe 2 as a detecting part. The optical sensor 23 is internally equipped with a small camera 24 using CCD (charge-coupled device), etc. and detects a part of the pattern formed on the acoustic coupler through the small camera 24. The pattern information detected by the optical sensor 23 is output to the position analyzing part 12 through a cable 25. If the cable 25 is not used, the pattern information may be transmitted to the position analyzing part 12 wirelessly.

For the ultrasonic probe 2 shown in FIG. 6, one optical sensor 23 is mounted on the side surface of the ultrasonic probe 2. The optical sensor 23 is mounted on the side surface of the case 21 of the ultrasonic probe 2, that is the side surface perpendicular to the arranged direction (scanning direction X in the figure) of the ultrasonic transducers 22. The position at which the optical sensor 23 is disposed corresponds with the position of a probe mark to be displayed on the display part 10.

For the ultrasonic probe shown in FIG. 6, only one optical sensor 23 is mounted on the ultrasonic probe 2. More than two optical sensors may be mounted on the ultrasonic probe 2 to detect the pattern formed on the acoustic coupler. By disposing a plurality of optical sensors to detect the pattern at a plurality of spots, the accuracy of the position detection may be enhanced.

Further, as shown in FIG. 7A and FIG. 7B, two optical sensors 26A and 26B may be mounted on the side surface of the ultrasonic probe 2. In the examples shown in FIG. 7A and FIG. 7B, two optical sensors 26A and 26B have been installed within the case 21. As described, by internally installing the optical sensors in the case 21, signals from the optical sensors 26A and 26B may be accommodated in the cable designated for transmitting/receiving signals of ultrasonic waves. As in the optical sensor 23 shown in FIG. 6, the optical sensor 26A is internally equipped with a small camera 27A using CCD, etc., and the optical sensor 26B is also internally equipped with a small camera 27B using CCD, etc., in order to detect a part of the pattern formed on the acoustic coupler through the small cameras 27A and 27B.

In the ultrasonic probe shown in FIG. 7A and FIG. 7B, the optical sensor 26A and the optical sensor 26B have been mounted on the side surfaces of the ultrasonic probe 2, respectively, which are the side surfaces opposite each other. The optical sensor 26A is mounted on the side surface perpendicular to the arranged direction (scanning direction X in the figure) of the ultrasonic transducers 22, whereas, the optical sensor 26B is mounted on the side surface of the opposite side of the side surface where the optical sensor 26A has been mounted. The position at which the optical sensor 26A has been mounted and the position of one end of a probe mark to be displayed on the display part 10 correspond to each other, while the position at which the optical sensor 26B has been mounted and the position of the end of the opposite side of the one end thereof correspond to each other.

The local pattern information detected by the optical sensors 26A and 26B is output to the position analyzing part 12 through a cable (not shown in the figure). Otherwise, the pattern information may also be transmitted to the position analyzing part 12 wirelessly. In the example shown in FIG. 7A and FIG. 7B, the pattern detected by the optical sensor 26A and the pattern detected by the optical sensor 26B differ in their patterns, and therefore, the respective position of the optical sensors 26A and 26B may be specified by the position analyzing part 12.

Position Analyzing Part

The position analyzing part 12 shown in FIG. 3 receives the local pattern information detected by the optical sensor 23, or by the optical sensors 26A and 26B, and further reads the information of the pattern formed at the acoustic couplers 30A, 30B, or 30C from the storage part 11. Then, by referring to the patterns stored in the storage 11, the position analyzing part 12 specifies the position (coordinate) of the local pattern detected by the optical sensor 23, or by the optical sensors 26A and 26B. That is, by matching the local pattern detected by the optical sensor 23, etc. and the pattern stored in the storage part 11, the position analyzing part 12 obtains the position (coordinate) of the local pattern on a pattern stored in the storage part 11. Moreover, the position analyzing part 12 outputs the information (coordinate information) indicating the position on the pattern to the display control part 9. Also, by linking the coordinate system of a body mark to be displayed on the display part 10 and the coordinate system of a pattern formed on the acoustic coupler 30A, etc., the coordinate on the pattern obtained by the position analyzing part 12 corresponds with the coordinate on the body mark.

Furthermore, the position analyzing part 12 comprising hardware may execute a function specifying a position and is equipped with a calculating device such as CPU, and also, by reading a position analyzing program stored in the storage part 11 and executing the same, the function of specifying the position may be executed.

The display control part 9 receives ultrasonic image data such as B-mode tomographic image data, etc. from the image generating part 8 and displays the ultrasonic image based on the ultrasonic image data on the display part 10. Further, the display control part 9 reads a body mark and a probe mark from the storage part 11 and displays the probe mark on the body mark in an overlapping manner on the display part 10. Then, the display control part 9 displays the probe mark on the body mark in an overlapping manner on the display part 10 at the position (coordinate) obtained by the position analyzing part 12.

Moreover, the display control part 9 may also display character information or graduation over the ultrasonic image on the display part 10.

Display Part

Figure 8:
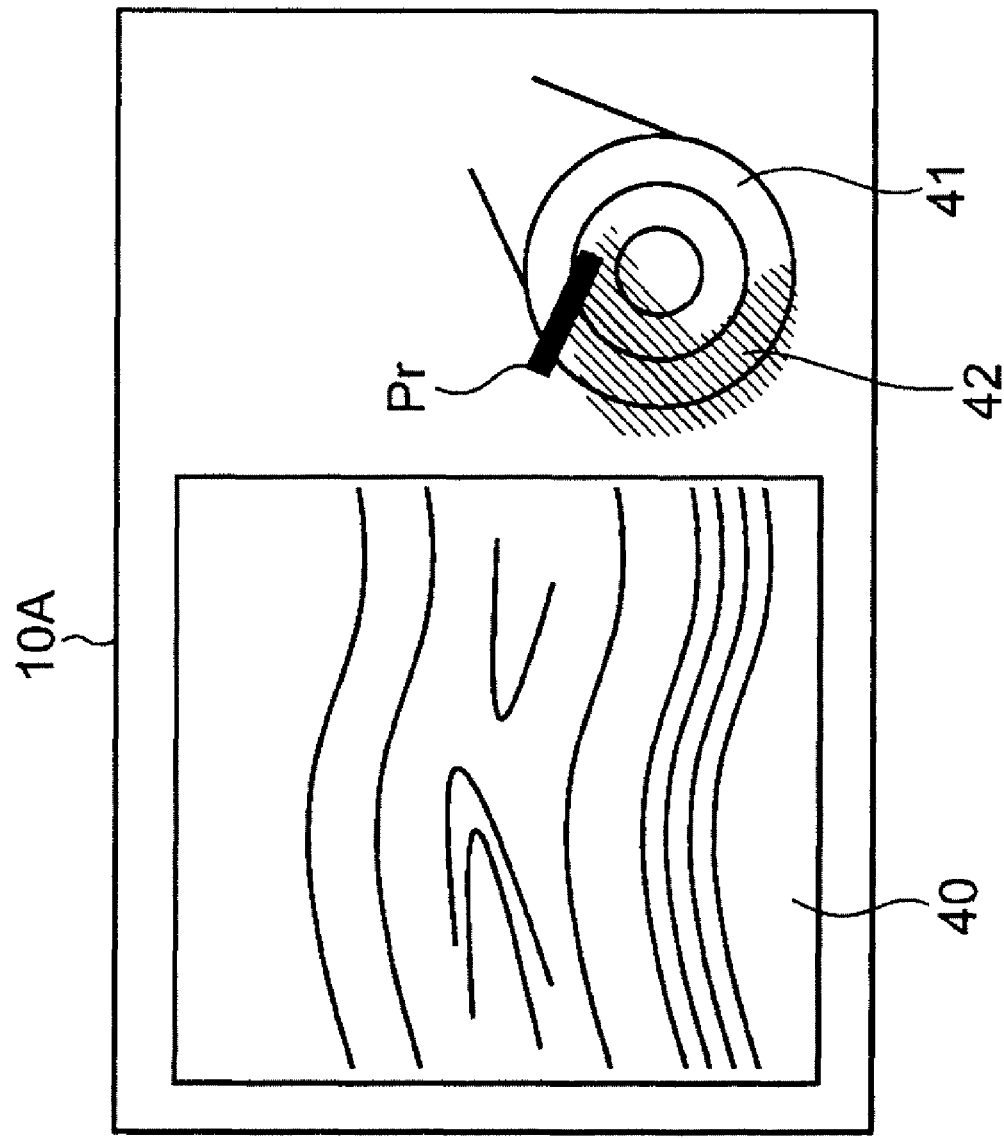
FIG. 8 is a diagram of a screen showing one example of an image and a body mark to be displayed on a display part.

On the display part 10, for example, a tomographic image and a body mark are displayed. An example of this display is described with reference to FIG. 8. FIG. 8 is a diagram of a screen showing an example of an image and a body mark to be displayed on the display part.

On the display part 10, a tomographic image 40 of a diagnostic part and a body mark 41 representing the diagnostic part are displayed. For example, when diagnosing a breast, a body mark 41 representing the breast is displayed on the monitor screen 10A, and also a probe mark Pr indicating the position of the ultrasonic probe 2 is displayed on the body mark 41. Since the body mark 41 expresses the subject to be examined (breast) P and the probe mark Pr expresses the ultrasonic probe 2, by displaying the probe mark Pr on the body mark 41, the positional relation between the subject to be examined (breast) P and the ultrasonic probe 2 will be displayed on the display part 10.

In the first embodiment, the probe mark Pr is rectangular-shaped, representing the position of the ultrasonic probe 2 on the acoustic coupler 30A. Upon receipt of the position information (coordinate information) on the body mark 41 from the position analyzing part 12, the display control part 9 displays the probe mark Pr at the position.

The probe mark Pr represents the position of the ultrasonic probe 2 on the acoustic coupler 30A. Since the acoustic coupler 30A is disposed on the subject to be examined (breast) P, it is presumed that the probe mark Pr represents the position of the ultrasonic probe 2 on the subject to be examined (breast) P. Then, by referring to the position of the probe mark Pr on the body mark 41, the position where the tomographic image 40 has been obtained (position scanned by the ultrasonic probe 2) may be easily captured.

By moving the ultrasonic probe 2, since the local patterns detected by the optical sensor 23 differ, the probe mark Pr will be displayed at the obtained position based on the local pattern information. That is, along with the movement of the ultrasonic probe 2, the position of the probe mark Pr on the body mark 41 moves. As a result, it becomes possible to easily capture the position (position scanned by the ultrasonic probe 2) where ultrasonic images such as tomographic image 40 displayed on the monitor screen 10A have been obtained.

Probe Mark

Moreover, as shown in FIG. 7A and FIG. 7B, when two optical sensors are provided with the ultrasonic probe 2, the position of an end part of the probe mark Pr and the position of one of the optical sensors correspond, while the position of the other end part of the probe mark Pr and the position of the other optical sensor correspond. From this, the orientation of the ultrasonic probe 2 may be specified.

Figure 9:
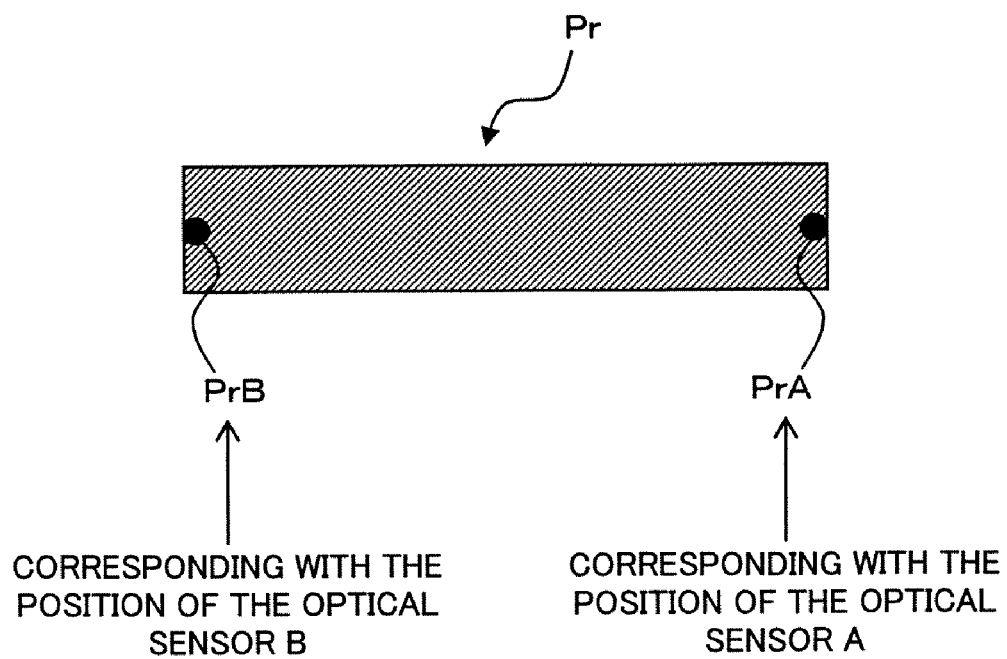
FIG. 9 is a schematic drawing of the positional relation between probe marks and optical sensors.

For example, as shown in FIG. 9, the position of the marked end part PrA of the probe mark Pr corresponds with the position of the optical sensor 26A, while the position of the mark end part PrB corresponds with the position of the optical sensor 26B. Based on the local pattern detected by the optical sensor 26A, the position of the optical sensor 26A on the acoustic coupler 30A may be specified, and the position corresponds with the position of the mark end part PrA on the body mark 41. Also, based on the local pattern detected by the optical sensor 26B, the position of the optical sensor 26B on the acoustic coupler 30A may be specified, and the position corresponds with the position of the marked end part PrB on the body mark 41.

As described, the position of the ultrasonic probe 2 may be specified by a plurality of optical sensors to make it possible to display the probe mark Pr on the display part 10 in accordance with the orientation of the ultrasonic probe 2.

Further, by differentiating the patterns formed at the acoustic couplers 30A, 30B and 30C for the left and the right of the breasts, the breast being subjected to diagnosis may be specified. For example, a pattern for the right is formed for the acoustic coupler to be put on the right breast and a pattern for the left is formed for the acoustic coupler to be put on the left breast, in order to form different patterns for the right and the left. In the information indicating the pattern for the right, the identifying information indicating the use for the right is added and stored in the storage part 11, and in the information indicating the pattern for the left, the identifying information indicating the use for the left is added and stored in the storage part 11.

Then, the position analyzing part 12 specifies the position of the ultrasonic probe 2 on the acoustic coupler 30A by comparing the local pattern detected by the optical sensor 23 and the patterns stored in the storage part 11. Then, by differentiating the patterns for the right pattern and for the left pattern, and by comparing the local pattern detected by the optical sensor 23 and the pattern either for the right or for the left stored in the storage part 11, the left or the right breast is also specified along with the position of the ultrasonic probe 2 on the acoustic coupler 30A.

As described, by the position analyzing part 12, the information indicating the position of the ultrasonic probe 2 on the acoustic coupler 30A (coordinate information) and the information indicating either the right breast or the left breast that is the subject of the diagnosis are obtained. The position analyzing part 12 outputs information indicating the right or the left of the breasts to the display control part 9 along with the information indicating the position (coordinate information) of the ultrasonic probe 2 on the acoustic coupler 30A.

Then, for example, upon receipt of the information indicating the left breast from the position analyzing part 12, the display control part 9 reads the body mark for the left breast from the storage part 11, displays the body mark for the left breast on the display part 10, and further displays the probe mark in an overlapping manner at the position (coordinate) obtained by the position analyzing part 12. Moreover, upon receipt of the information indicating the right breast from the position analyzing part 12, the display control part 9 reads the body mark for the right breast from the storage part 11, displays the body mark for the right breast on the display part 10, and further displays the probe mark in an overlapping manner at the position (coordinate) obtained by the position analyzing part 12. As described, by preparing a pattern for the right and a pattern for the left, either the left or the right may automatically be specified.

Moreover, as shown in FIG. 8, based on the position specified by the position analyzing part 12, the moved trace 42 of the ultrasonic probe 2 may also be displayed on the body mark 41. For example, the display control part 9 displays the color of the range where the probe mark Pr has been displayed on the body mark 41 by tinting with a color different from the color of the range where it has not been displayed yet for a display on the display part 10. As a result, the color of the range where the ultrasonic probe 2 has passed and the color of the range where it has not yet passed are distinguished and displayed, and thus, the range where the ultrasonic probe 2 has passed may easily be captured. That is, by tinting the color of the range where the probe mark Pr has passed with a color different from that of the range where it has not yet passed, the range examined by the ultrasonic probe 2 and unexamined range may easily be distinguished; thus, making it possible to easily capture the examined range or the unexamined range.

Also, the timing of drawing the trace may be made controllable to prevent the trace from being displayed when the operator accidentally applies the ultrasonic probe 2 onto the subject to be examined (breast) P. For example, by providing an examination button for the inputting part 15 and by pressing down the examination button, the operator may switch drawing start or drawing stop of the probe mark or the trace.

To be more precise, when the operator presses down the examination button, the signal corresponding to the pressing is output to the control part 13. Upon receipt of the signal, the control part 13 outputs an instruction to start drawing to the display control part 9. Upon receipt of the instruction to start drawing from the control part 13, the display control part 9 displays the probe mark and the trace on the display part 10. Then, once again when the examination button is pressed, the control part 13 outputs an instruction to stop drawing to the display control part 9, and upon receipt of the instruction to stop drawing from the control part 13, the display control part 9 stops drawing the probe mark and the trace. As described, by instructing the drawing timing through the operator, drawing of unintended traces becomes preventable.

Also, pattern detecting by the optical sensor 23 may be started or stopped by the operator pressing down the examination button. In this case, when the examination button is pressed down by the operator, the control part 13 outputs an instruction to the optical sensor 23 to begin the examination. Upon receipt of the instruction to begin the examination, the optical sensor 23 detects the pattern formed at the acoustic coupler, and outputs the pattern information to the position analyzing part 12. Then, the matching process is performed by the position analyzing part 12 to specify the position of the ultrasonic probe 2 and the position is displayed on the display part 10. Subsequently, if the examination button is once again pressed down, the control part 13 outputs an instruction to end the examination to the optical sensor 23. Upon receipt of the instruction to end the examination, the optical sensor 23 stops detecting the pattern. As described, by controlling the pattern detecting of the optical sensor 23, drawing of unintended traces becomes preventable.

Moreover, by designating a foot switch as an examination button to operate the foot switch by foot or by providing an examination button for the ultrasonic probe 2, the operator may easily instruct the drawing timing. As a result, the examination may be conducted without obstructing the examination.

Operation

Figure 10:
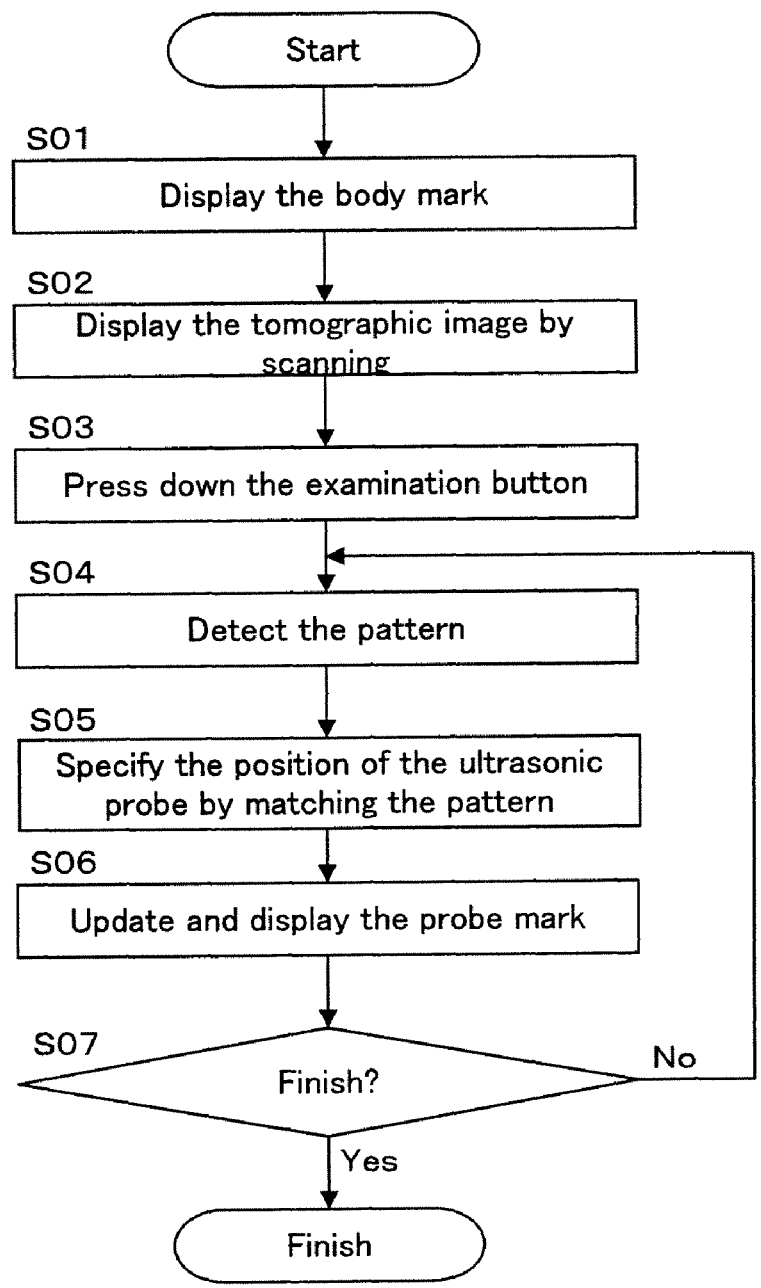
FIG. 10 is a flow chart showing a series of operations performed by the ultrasonic imaging apparatus related to the first embodiment of the present invention.

Next, referring to FIG. 10, the operation of the ultrasonic imaging apparatus related to the first embodiment of the present invention is described. FIG. 10 is a flow chart showing a series of operations conducted by the ultrasonic imaging apparatus related to the first embodiment of the present invention.

Before conducting the examination, an acoustic coupler 30A, 30B or 30C is put on the patient. When diagnosing breasts, the acoustic coupler 30A, 30B or 30C is put on the breasts. As with the acoustic coupler 30C, in the event of using an acoustic coupler that can be hung on the shoulder, the patient is able to put on the acoustic coupler 30C in a changing room and similar facilities, hence making it possible to be examined without exposing the breasts.

(Step S01)

First, the body mark representing the part to be examined is displayed on the display part 10. For example, when diagnosing breasts, the operator designates a body mark representing breasts using the inputting part 15, and the display control part 9 then reads the body mark for breasts from body marks stored in the storage part 11 and displays the body mark for breasts on the display part 10.

(Step S02)

Next, the operator makes the ultrasonic probe 2 contact the acoustic coupler 30A. Then, ultrasonic waves are transmitted by the ultrasonic probe 2 to generate B-mode tomographic image data based on the received reflection waves, and the tomographic image is displayed on the display part 10.

(Step S03)

Next, the operator gives an instruction to begin the examination at a desired timing. For example, by pressing down the examination button provided with the inputting part 15, the instruction to begin the examination is given to the ultrasonic imaging apparatus.

(Step S04)

When the instruction to begin the examination is given, the pattern formed at the acoustic coupler 30A is detected by the optical sensor 23 and the information indicating the pattern to the position analyzing part 12 is output.

Further, in the first embodiment, when the instruction to start the examination is given, the pattern of the acoustic coupler 30A is detected by the optical sensor 23 and the pattern information is output to the position analyzing part 12; however, the pattern of the acoustic coupler 30A may be detected by the optical sensor 23 and be output to the position analyzing part 12 without waiting for the instruction to begin the examination.

(Step S05)

Upon receipt of the information indicating the pattern from the optical sensor 23, the position analyzing part 12 reads the information indicating the pattern formed at the acoustic coupler 30A from the storage part 11, and specifies the position (coordinate) of the pattern detected by the optical sensor 23 by matching the pattern received from the optical sensor 23 and the pattern stored in the storage part 11. This position (coordinate) represents the position (coordinate) of the ultrasonic probe 2 on the acoustic coupler 30A. The position analyzing part 12 outputs the information indicating the position (coordinate information) to the display control part 9.

(Step S06)

Upon receipt of the information indicating the position (coordinate information) of the ultrasonic probe 2 from the position analyzing part 12, the display control part 9 displays the probe mark on the body mark in an overlapping manner on the display part 10 at the position (coordinate) specified by the position analyzing part 12.

For example, as shown in FIG. 8, the display control part 9 displays a tomographic image 40 and a body mark 41 on the monitor screen 10A of the display part 10. Further, the display control part 9 displays a probe mark Pr representing the ultrasonic probe 2 on the body mark 41 at the position (coordinate) obtained by the position analyzing part 12. Through this, the position where the tomographic image has been acquired is automatically obtained and displayed on the display part 10.

(Step S07)

Also, to end the examination, the operator gives an instruction to end the examination at a desired timing. For example, by once again pressing down the examination button provided with the inputting part 15, the instruction to end the examination is given to the ultrasonic imaging apparatus. When the instruction to end the examination is given (S07, Yes), the updating of the probe mark Pr stops. Whereas, if the instruction to end the examination is not given (Step S07, No), the operations of Step S04 through Step S06 is repeatedly executed, and accompanied by the movement of the ultrasonic probe 2, the probe mark Pr moves onto the body mark 41 to be displayed.

In the case of not ending the examination (Step S07, No), based on the pattern that has been newly detected by the optical sensor 23, the position (coordinate) of the ultrasonic probe 2 on the acoustic coupler 30A is specified, and the probe mark Pr is displayed on the body mark 41 in accordance with the information indicating the position (coordinate information). Also, along with the movement of the probe mark Pr, the display control part 9 displays the moved range of the probe mark Pr on the display part 10 by tainting with a color that is different from that of the other range. As a result, the range scanned by the ultrasonic probe 2 and the range that has not been scanned yet may be easily distinguished.

Other than displaying the information indicating the position of the ultrasonic probe 2 on the body mark 41 as probe mark Pr, in addition to recording the ultrasonic image, the information (coordinate information) indicating the position of the ultrasonic probe 2 may be recorded as associated information of the ultrasonic image. For example, the figure information indicating the body mark 41, probe mark Pr and trace 42 being displayed on the monitor screen 10A of FIG. 8 is recorded in the storage part 11 as is. As a result, when the ultrasonic image is read out for the diagnostic reading, the probe mark Pr indicating the position where the ultrasonic image has been obtained is displayed on the body mark 41; thus, making it easier to capture the position where the ultrasonic image has been obtained.

Furthermore, by automatically recording the position of the ultrasonic probe 2, forgetting to attach the probe mark Pr to the body mark 41 or attaching the probe mark Pr to a wrong position becomes preventable. Moreover, the probe mark Pr is automatically attached, making it possible to reduce the time for the operator to attach the probe mark Pr. As a result, in case of examining a large number of patients, the operator's load may be eased, and the time for the examination may also be reduced.

In addition, the coordinate information of the probe mark Pr on the body mark 41 may be stored in the storage part 11. Through this, the position of the ultrasonic probe 2 on the acoustic coupler 30A is stored. Moreover, when an ultrasonic image for the diagnostic reading is read out, the coordinate information is displayed on the body mark 41, making it easier to capture the position where the ultrasonic image has been obtained. Moreover, whether the positional information is to be displayed or not to be displayed may be selected by the operator.

For example, by designating the center of the body mark 41 as the center of the polar coordinate system, the angle (direction) where the probe mark Pr is being displayed and the distance from the center to the probe mark Pr are recorded in the storage part 11. Since the center of the body mark 41 corresponds with the center of the acoustic coupler 30A, regarding the center of the acoustic coupler 30A as the center of the polar coordinate system, the angle (direction) where the ultrasonic probe 2 is disposed and the distance from the center to the ultrasonic probe 2 will be recorded.

To be precise, by designating the center of the body mark 41 as the center of the clock, the time (direction) where the probe mark Pr is being displayed and the distance from the center to the probe mark Pr are recorded. Since the center of the body mark 41 corresponds with the center of the acoustic coupler 30A, regarding the center of the acoustic coupler 30A as the center of the clock, the time (direction) where the ultrasonic probe 2 is disposed and the distance from the center to the ultrasonic probe 2 are recorded.

Further, when the breasts are examined, in addition to recording the position information of the ultrasonic probe 2, the information indicating the left or the right breast may also be recorded in the storage part 11.

Furthermore, according to the level of the reflection waves received by the ultrasonic probe 2, drawing of the probe mark Pr and the trace may be stopped. For example, upon receipt of signals output from the receiving part 4, a determining part (not illustrated) is provided for determining whether the ultrasonic probe 2 is away from the acoustic coupler or not. For example, if the signals output from the receiving part 4 drop to the preliminarily set signal level or below, e.g. below noise level, then the ultrasonic probe 2 is determined to be away from the acoustic coupler.

When it is determined that the ultrasonic probe 2 is away from the acoustic coupler, the determining part outputs the determined result to the control part 13. Upon receipt of the determined result, the control part 13 outputs an instruction to stop drawing to the display control part 9. Upon receipt of the instruction to stop drawing, the display control part 9 stops drawing of the probe mark Pr and the trace. As a result, drawing and recording of unintended traces become preventable.

Moreover, upon receipt of the determined result from the determining part, the control part 13 may also output an instruction to end the examination to the optical sensor 23. Upon receipt of the instruction to end the examination, the optical sensor 23 stops detecting patterns. As a result, drawing and recording of unintended traces become preventable.

Detecting the Inclination of the Ultrasonic Probe

Figure 11:
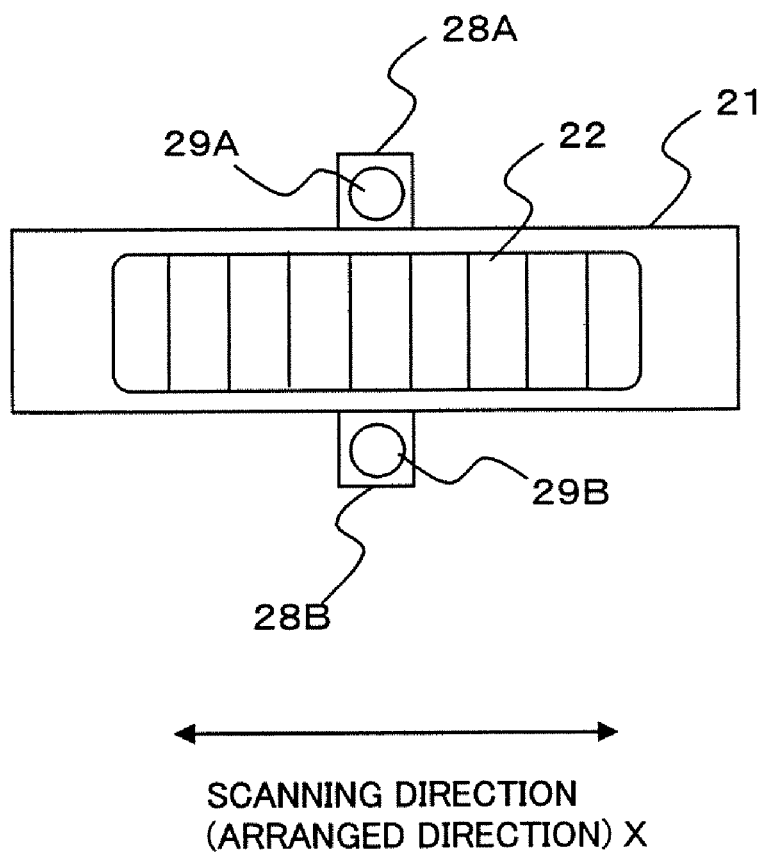
FIG. 11 is a plane drawing showing another ultrasonic probe and optical sensors used in the ultrasonic imaging apparatus related to the first embodiment of the present invention.

Next, the method of detecting the inclination of the ultrasonic probe 2 is described with reference to FIG. 11. FIG. 11 is a plane drawing showing another ultrasonic probe and optical sensors used in the ultrasonic imaging apparatus related to the first embodiment of the invention.

As shown in FIG. 11, two optical sensors, namely optical sensor 28A and optical sensor 28B, are mounted respectively on the side surfaces of the ultrasonic probe 2, that is, the side surfaces opposite each other. To be more precise, the optical sensor 28A has been mounted on the side surface parallel to the arranged direction (scanning direction X in the figure) of the ultrasonic transducers 22, whereas the optical sensor 28B has been mounted on the side surface of the opposite side of the side surface where the optical sensor 28A has been mounted.

Further, optical sensors 28A and 28B may also be disposed in the case 21, or be disposed on the external part of the case 21.

Similar to the optical sensor 23 shown in FIG. 6, the optical sensor 28A is internally equipped with a small camera 29A using CCD, etc., and likewise, the optical sensor 28B is also internally equipped with a small camera 29B using CCD, etc., in order to detect a part of the pattern formed on an acoustic coupler through the small camera 29A and 29B.

The local pattern information detected by the optical sensors 28A and 28B is output to the position analyzing part 12 through a cable (not illustrated). In the example shown in FIG. 11, the pattern detected by the optical sensor 28A and the pattern detected by the optical sensor 28B differ in their patterns, and therefore, the respective positions of the optical sensors 28A and 28B may be specified by the position analyzing part 12.

As in the process described above, the position analyzing part 12 determines the position (coordinate) of the local pattern on a pattern stored in the storage part 11 by matching the local pattern detected by the optical sensors 28A and 29B and the pattern stored in the storage part 11. Also, the position analyzing part 12 outputs the information (coordinate information) showing the position of the pattern to the display control part 9. The display control part 9 displays the probe mark on the body mark in an overlapping manner on the display part 10 at the position (coordinate) determined by the position analyzing part 12.

Further, if the optical sensors 28A and 28B are arranged as shown in FIG. 11, the position analyzing part 12 calculates the inclination of the ultrasonic probe 2. For example, if the ultrasonic probe 2 has been disposed parallel to the subject to be examined, the amount of light detected by the optical sensor 28A and the amount of light detected by the optical sensor 28B would be the same. If the ultrasonic probe is disposed in a parallel pattern, the distance between the optical sensor 28A and the subject to be examined, and the distance between the optical sensor 28B and the subject to be examined would be the same, and, accordingly, the amount of light received by the optical sensors 28A and 28B would be equal.

Whereas, if the ultrasonic probe 2 is inclined in the direction perpendicular to the scanning direction X, the distance between the optical sensor 28A and the subject to be examined, and the distance between the optical sensor 28B and the subject to be examined would not be equal, and hence, the amount of light received by the optical sensor 28A and the amount of light received by the optical sensor 28B would be different.

The position analyzing part 12 compares the amount of light received by the optical sensor 28A and the amount of light received by the optical sensor 28B to determine the inclination angle of the ultrasonic probe 2 in the direction perpendicular to the scanning direction X.

Upon receipt of the information indicating the inclination angle of the ultrasonic probe from the position analyzing part 12, the display control part 9 allows the display part 10 to display the angle expressing the inclination of the ultrasonic probe as well as the position of the ultrasonic probe Embodiment 2

Figure 12:
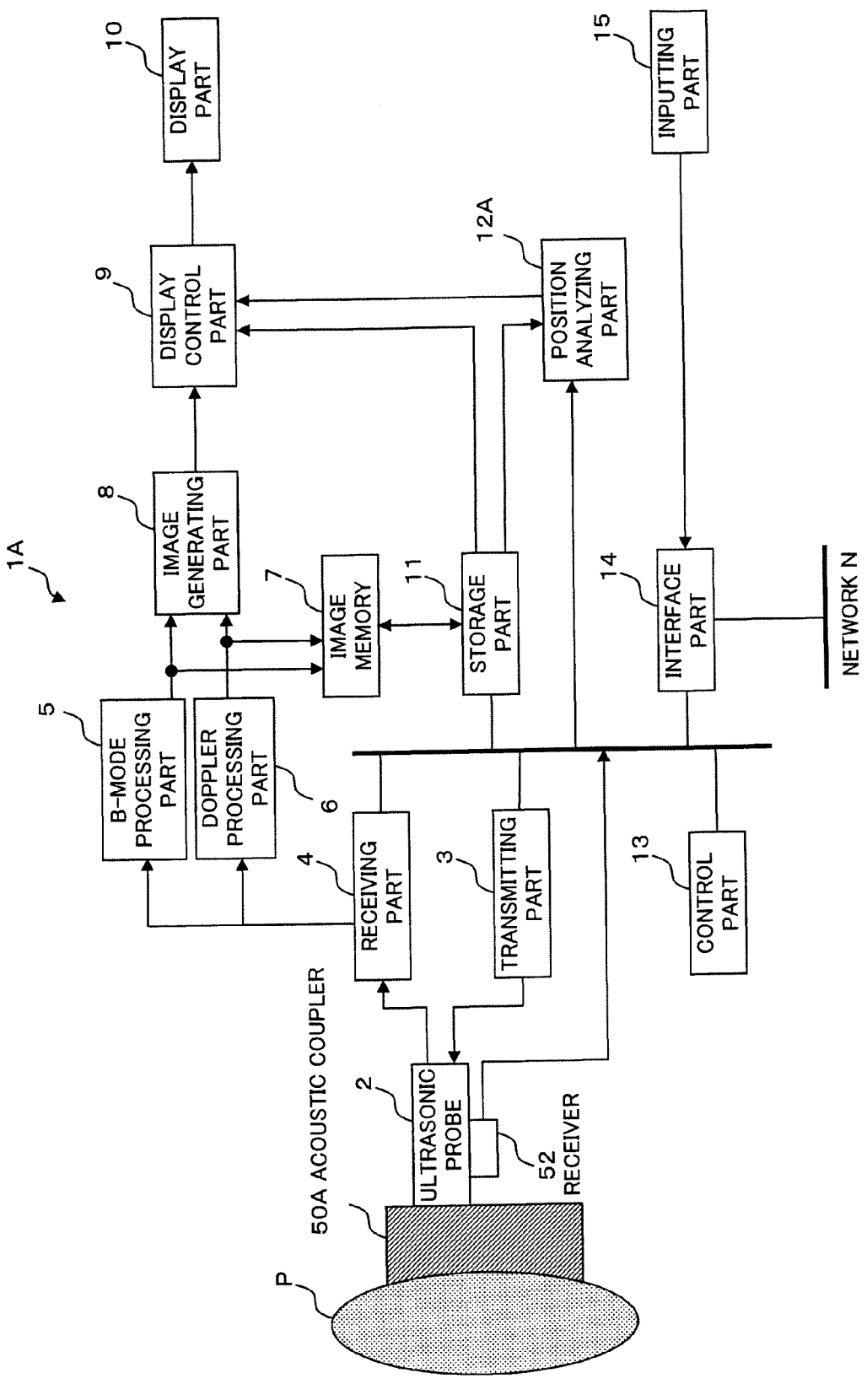
FIG. 12 is a block diagram showing the ultrasonic imaging apparatus related to the second embodiment of the present invention.
Figure 13:
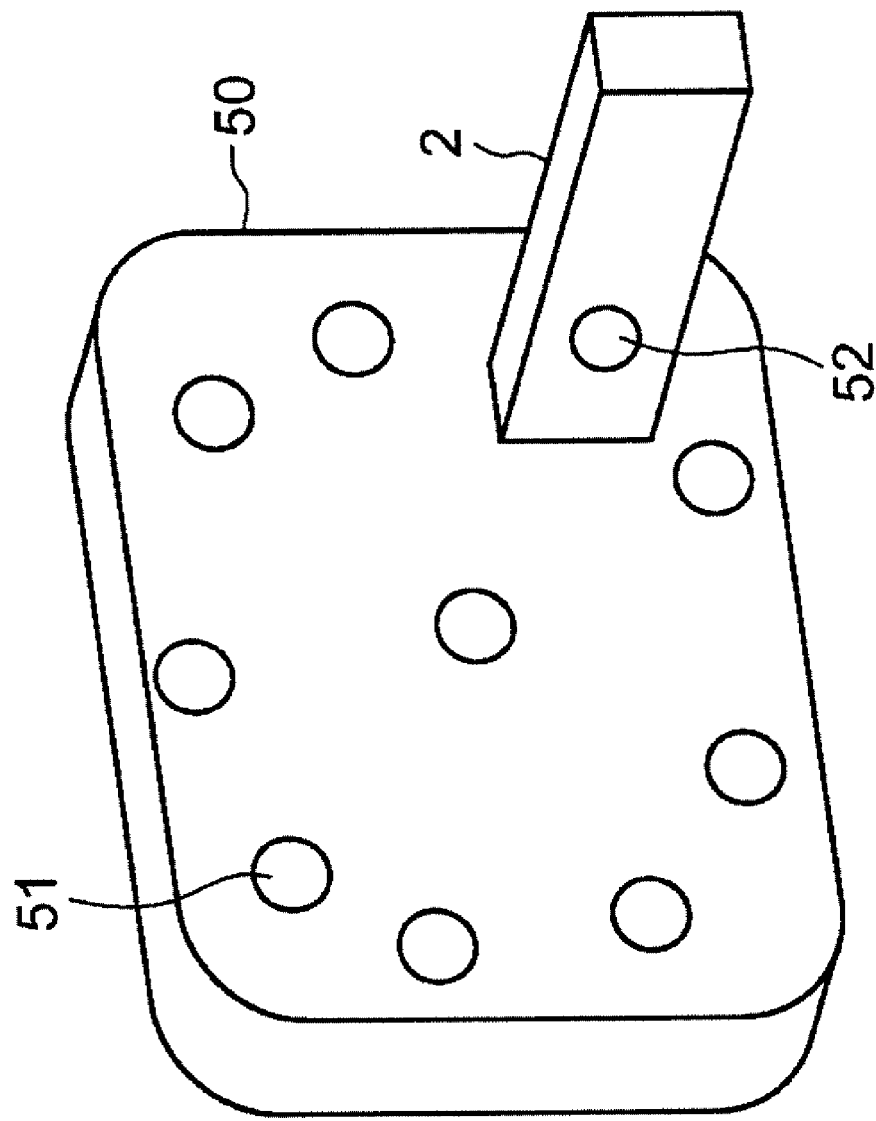
FIG. 13 is an oblique view showing an acoustic coupler used in the ultrasonic imaging apparatus related to the second embodiment of the present invention.

Next, an ultrasonic imaging apparatus related to the second embodiment of the present invention is described with reference to FIG. 12 and FIG. 13. FIG. 12 is a block diagram showing the ultrasonic imaging apparatus related to the second embodiment of the present invention. FIG. 13 is an oblique view of an acoustic coupler used in the ultrasonic imaging apparatus related to the second embodiment of the present invention.

In the second embodiment, in place of acoustic couplers 30A, 30B and 30C related to the first embodiment, an acoustic coupler 50 is used. Further, the ultrasonic imaging apparatus 1A related to the second embodiment is provided with another position analyzing part 12A in place of a position analyzing part 12. Moreover, in place of an optical sensor 23, a receiver 52 is disposed in the ultrasonic probe 2. As for the constitution, with the exception of the acoustic coupler 50, the position analyzing part 12A and the receiver 52, the constitution is the same as that of ultrasonic imaging apparatus related to the first embodiment, and hence, a description is omitted. Hereinafter, the constitution of the acoustic coupler 50, the function of the position analyzing part 12A and the function of the receiver 52 is described.

As shown in FIG. 13, as a transmitting part, a plurality of small radio frequency identifications: RFID 51 have been embedded in the acoustic coupler 50 related to the second embodiment. In the individual RFID 51, unique ID information (identifying information) has been stored respectively, and the ID information is transmitted. In the storage part 11, the ID information (identifying information) of individual RFID 51 and the information (coordinate information) indicating the position of the individual RFID 51 on the acoustic coupler 50 have been linked and stored.

The receiver 52 for detecting the ID information of the RFID 51 is disposed in the ultrasonic probe 2. When an operator scans the ultrasonic probe 2 on the surface of the acoustic coupler 50, the receiver 52 receives the ID information being transmitted from the RFID 51 located in the most proximal position. The ID information received by the receiver 52 is output to the position analyzing part 12A.

For example, when the same level of signals are transmitted by each RFID 51, among a plurality of received signals, the receiver 52 outputs the ID information of the RFID 51 that has transmitted the highest level of signals to the position analyzing part 12A. The RFID 51 that has transmitted the highest level of signals is considered to exist at the position most proximal to the ultrasonic probe 2, and the RFID 51 is considered to be corresponding to the position of the ultrasonic probe 2.

Upon receipt of the ID information from the receiver 52, referring to the linkage of the ID information of the RFID 51 stored in the storage 11 and the information indicating the position (coordinate information), the position analyzing part 12A specifies the position (coordinate) of the RFID 51 attached with the ID information. This position (coordinate) is the equivalent of the position (coordinate) of the ultrasonic probe 2 on the acoustic coupler 50. The position analyzing part 12A outputs the information indicating the position (coordinate information) of the ultrasonic probe 2 to the display control part 9.

As in the first embodiment, the display control part 9 reads a body mark from the storage part 11, and on the body mark a probe mark is overlapped to be displayed on the display part 10. Then, the display control part 9 displays the probe mark on the body mark in an overlapping manner on the display part 10 at the position (coordinate) determined by the position analyzing part 12A. On the display part 10, similar to the ultrasonic imaging apparatus related to the first embodiment, ultrasonic images such as tomographic images and a body mark are displayed, and on the body mark, a probe mark indicating the position of the ultrasonic probe 2 is displayed.

As described, by using the RFID 51 to transmit unique ID information (identifying information), the position of the ultrasonic probe 2 on the acoustic coupler 50 may be specified, making it possible for the operator to easily capture the position where the ultrasonic image has been obtained.

Further, also in the second embodiment, as in the first embodiment, by assigning a different pattern for the arranged pattern of the RFID 51 respectively for the left and the right breasts, it becomes possible to specify the breast being subjected to diagnosis. Moreover, as in the first embodiment, based on the position of the ultrasonic probe 2 specified by the position analyzing part 12A, the moved trace of the ultrasonic probe 2 may also be displayed on the body mark. Furthermore, in addition to recording the ultrasonic image, the information indicating the position (coordinate position) of the ultrasonic probe 2 may also be recorded as associated information of the ultrasonic image. In this case, figure information representing the body mark, probe mark and trace may be recorded as is, and the coordinate information of the ultrasonic probe 2 on the acoustic coupler 50 may also be recorded.

Modification Example

Figure 14:
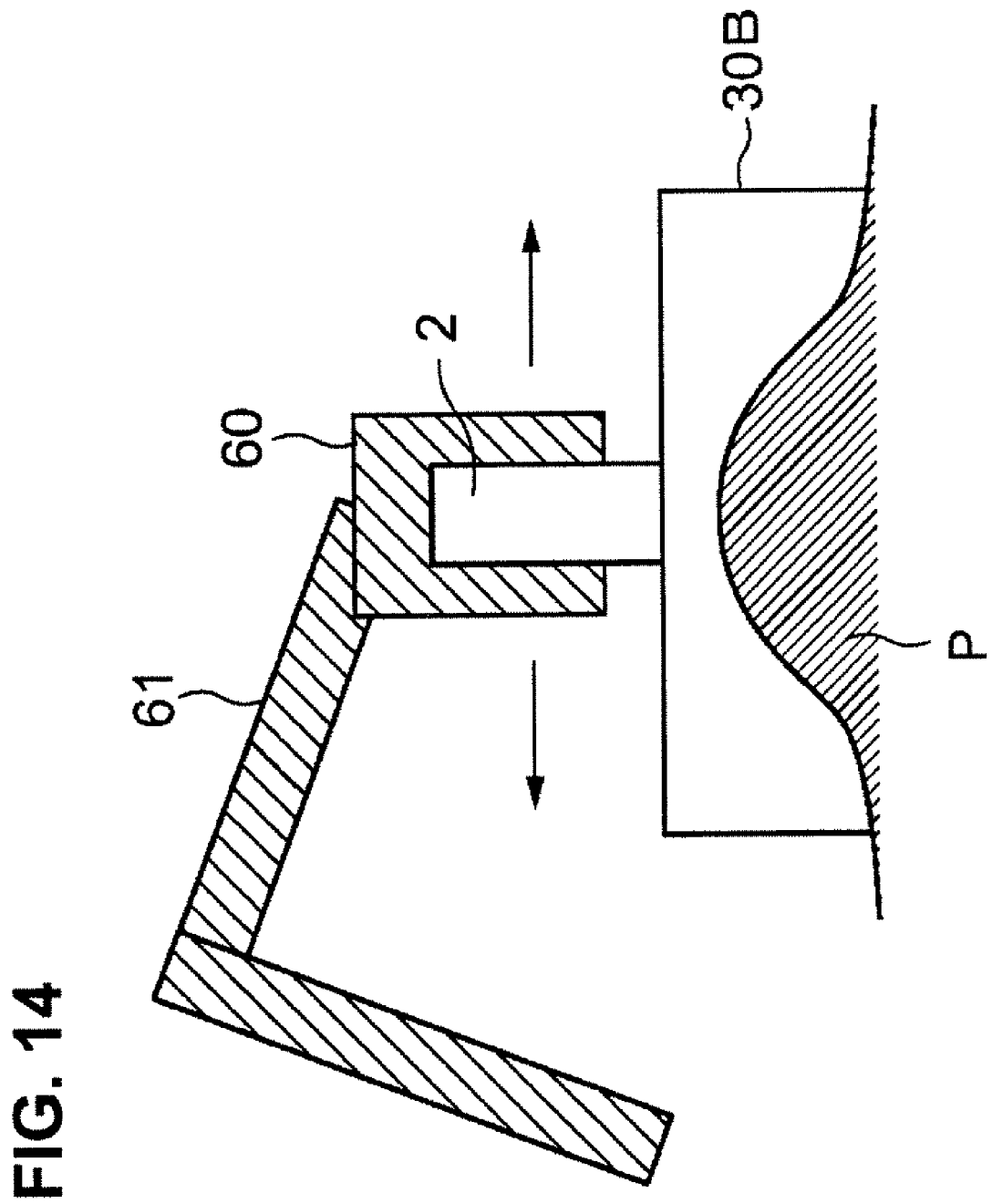
FIG. 14 is a cross-sectional drawing showing an ultrasonic probe related to the modification example.

Next, a modification example of the ultrasonic probe related to the first embodiment and the second embodiment described above is described referring to FIG. 14. FIG. 14 is a side view of an ultrasonic probe related to the modification example. As in the first embodiment or in the second embodiment, the ultrasonic probe 2 related to the modification example is provided with an optical sensor 23 or a receiver 52. Moreover, as an acoustic coupler, as in the first embodiment or second embodiment, an acoustic coupler 30A, 30B, 30C, or an acoustic coupler 50 is used.

Similar to the first embodiment, as an acoustic coupler, when the acoustic coupler 30A, 30B or 30C where the prescribed pattern has been formed is used, by mounting the optical sensor 23 on the ultrasonic probe 2, the pattern that has been formed at the acoustic coupler 30A, 30B or 30C is detected by the optical sensor 23, and the information indicating the pattern is output to the position analyzing part 12. As in the first embodiment, the position analyzing part 12 specifies the position (coordinate) of the ultrasonic probe 2 on the acoustic coupler 30A, 30B, or 30C.

Whereas, similar to the second embodiment, when the acoustic coupler 50 provided with the RFID 51 is used as an acoustic coupler, a receiver 52 is disposed in the ultrasonic probe 2, the ID information of the RFID 51 provided with the acoustic coupler 50 is received by the receiver 52 and the ID information that has been received is output to the position analyzing part 12A shown in FIG. 12. The position analyzing part 12A specifies the position (coordinate) of the ultrasonic probe 2 on the acoustic coupler 50, as in the second embodiment.

In this modification example, the ultrasonic probe 2 is being supported with both of its side surfaces sandwiched by a supporting member 60. To the supporting member 60, a mechanical arm 61 is connected through a joint member (not illustrated). By moving the arm 61 through a driving part (not illustrated), the supporting member 60 may be moved in the direction of choice. This makes it possible to move the ultrasonic probe 2 being supported by the supporting member 60 in the direction of choice on an acoustic coupler while maintaining contact with the acoustic coupler. Further, the supporting member 60, arm 61, and driving part are examples of a moving part for moving the ultrasonic prove 2.

The movement of the arm 61 is controlled by the control part 13 shown in FIG. 3 or FIG. 12. The moving speed, moving distance, and moving direction, etc., of the arm 61 are preliminarily set, and the movement is made according to the prescribed program. Moreover, accompanied by the movement of the arm 61, the ultrasonic probe 2 is moved on the acoustic coupler 30A. For example, as an acoustic coupler, when the acoustic coupler 30A where the prescribed pattern has been formed is used, the pattern of the acoustic coupler 30A is detected by the optical sensor 23, and the position (coordinate) of the ultrasonic probe 2 on the acoustic coupler 30A is specified by the position analyzing part 12.

As described, by automatically scanning the ultrasonic probe 2 by the mechanically moving arm 61 in accordance with the prescribed program, since the same operation may be conducted for a different patient, the position where the tomographic image has been obtained may be estimated. Moreover, by forming a prescribed pattern on an acoustic coupler, or by providing an RFID, etc., to detect the position of the ultrasonic probe 2 in real time, it becomes possible to easily capture the position of the ultrasonic probe 2 (position where the ultrasonic image has been obtained).

What is claimed is:

1. An ultrasonic imaging apparatus comprising:
   an acoustic coupler, including a low attenuation medium, on which a prescribed pattern that is readable and whose shape is maintained is internally or superficially formed, the prescribed pattern having different arrangements corresponding to a position in the prescribed pattern;
   an ultrasonic probe arranged on the acoustic coupler and configured to transmit an ultrasound wave to a subject via the acoustic coupler;
   a storage part configured to preliminarily store a stored pattern constituting the prescribed pattern formed on the acoustic coupler;
   a detecting part mounted on said ultrasonic probe operable to detect a part of the prescribed pattern formed on the ultrasonic low attenuation medium of the acoustic coupler;
   a position analyzing part configured to specify a position of said ultrasonic probe on the acoustic coupler, by pattern matching on the detection results of said detecting part with reference to said stored pattern that has been preliminarily stored in the storage part to specify a stored pattern corresponding to the detection result; and
   a display control part configured to control a display part to display the positional relation between said ultrasonic probe and said subject to be examined, wherein the position of said ultrasonic probe on the acoustic coupler is specified from the specified stored pattern.

2. An ultrasonic imaging apparatus according to claim 1, wherein
   said prescribed pattern includes a plurality of regions, and the individual regions are stained with different colors respectively, and
   said detecting part detects a part of the pattern.

3. An ultrasonic imaging apparatus according to claim 1, wherein
   said prescribed pattern includes white block-shaped patterns and black block-shaped patterns, and
   said detecting part detects a part of the pattern.

4. An ultrasonic imaging apparatus according to claim 1, wherein
   said prescribed pattern includes two-dimensional codes divided into a plurality of regions, and
   said detecting part detects a part of the pattern.

5. An ultrasonic imaging apparatus according to claim 1, wherein the acoustic coupler is to be arranged on breasts of said subject to be examined, and a different pattern is formed respectively for the left and right of said breasts.

6. An ultrasonic imaging apparatus according to claim 1, wherein
said display control part controls the display part to display the positional relation between said ultrasonic probe and said subject to be examined as well as the image of said subject to be examined which is obtained by said ultrasonic probe.

7. An ultrasonic imaging apparatus according to claim 1, further comprising:
a storage part for storing the positional relation between said ultrasonic probe and said subject to be examined with linkage to the image of said subject to be examined, obtained by said ultrasonic probe.

8. An ultrasonic imaging apparatus according to claim 1, wherein
said display control part controls the display part to display a schematic figure representing a part for imaging, and also to display a schematic figure representing said ultrasonic probe at a position corresponding to the position of said ultrasonic probe, within said schematic figure representing the part for imaging.

9. An ultrasonic imaging apparatus according to claim 8, wherein
said display control part controls the display part to display the portion in which said schematic figure representing the ultrasonic probe is displayed and other portions differently within said schematic figure representing the diagnostic part.

10. An ultrasonic imaging apparatus according to claim 9, wherein
said display control part controls the display part to stain said portion within the schematic figure representing the ultrasonic probe with a color different from other said portions.

11. An ultrasonic imaging apparatus according to claim 1, wherein
said display control part controls the display part to display the trace formed by the movement of said ultrasonic probe, based on the position of said ultrasonic probe which is specified by said position analyzing part.

12. An ultrasonic imaging apparatus according to claim 1, wherein
the acoustic coupler has a flat surface on the opposite side of the surface contacting said subject to be examined and said ultrasonic probe is disposed on said flat surface.

13. An ultrasonic imaging apparatus according to claim 1, wherein
the acoustic coupler is of a shape configured to cover breasts of said subject to be examined.

14. An ultrasonic imaging apparatus according to claim 13, wherein
the acoustic coupler includes shoulder straps.

15. An ultrasonic imaging apparatus according to claim 1, further comprising:
a moving part configured to move said ultrasonic probe on the acoustic coupler.

16. An ultrasonic imaging apparatus according to claim 1, wherein
said detecting part comprises a first optical sensor and a second optical sensor, said first optical sensor mounted on a side surface of said ultrasonic probe, said second optical sensor mounted on a side surface that is opposite to the side surface where said first optical sensor is mounted, and wherein
said position analyzing part specifies the position of said ultrasonic probe on the acoustic coupler, based on the detection results of said first optical sensor and said second optical sensor, and further determines the inclining angle of said ultrasonic probe in the direction perpendicular to a scanning direction, based on the difference of the amount of light detected by said first optical sensor and the amount of light detected by said second optical sensor, and
said display control part controls the display part to display the positional relation between said ultrasonic probe and said subject to be examined, and further to display the inclining angle of said ultrasonic probe on said display part.

17. An ultrasonic imaging apparatus comprising:
an acoustic coupler, including a low attenuation medium, on which a prescribed pattern that is readable and whose shape is maintained is internally and superficially formed, the prescribed pattern having different arrangements corresponding to a position in the prescribed pattern;
an ultrasonic probe arranged on the acoustic coupler and configured to transmit an ultrasound wave to a subject via the acoustic coupler;
a storage part configured to preliminarily store a stored pattern constituting the prescribed pattern formed on the acoustic coupler;
a detecting part mounted on said ultrasonic probe operable to detect a part of the prescribed pattern formed on the ultrasonic low attenuation medium of the acoustic coupler;
a plurality of transmitting parts, each of which is disposed on the acoustic coupler and configured to transmit unique identifying information;
a receiving part operable to receive the unique identifying information transmitted by the plurality of transmitting parts;
a position analyzing part configured to identify the position of said ultrasonic probe on the acoustic coupler, by pattern matching on the unique identifying information received by said receiving part with reference to said stored pattern that has been preliminarily stored in the storage part to specify a stored pattern corresponding to the detection result; and
a display control part configured to control the display part to display the positional relation between said ultrasonic probe and said subject to be examined, wherein the position of said ultrasonic probe on the acoustic coupler is specified from the specified stored pattern.

18. An ultrasonic low attenuation medium, comprising:
a prescribed pattern which is readable by a detecting part provided on an ultrasonic probe and that is internally or externally formed, wherein a surface of the ultrasonic probe is recessed.

19. An ultrasonic low attenuation medium according to claim 18, wherein
the ultrasonic low attenuation medium is of a shape to cover breasts of the subject to be examined.

20. An ultrasonic low attenuation medium according to claim 18, wherein
said prescribed pattern includes a plurality of regions, and the individual regions are stained with different colors.

21. An ultrasonic low attenuation medium according to claim 18, wherein
said prescribed pattern includes two-dimensional codes divided into a plurality of regions.

22. An ultrasonic low attenuation medium according to claim 18, wherein
the ultrasonic low attenuation medium is configured to be used for breasts of said subject to be examined, and a different pattern is formed respectively for the left and right said breasts.

23. An ultrasonic low attenuation medium according to claim 18, wherein
the ultrasonic low attenuation medium has a flat surface on the opposite side of the surface and said ultrasonic probe is arranged on said flat surface.

24. An ultrasonic imaging apparatus according to claim 1, wherein
said prescribed pattern includes a plurality of concentric circles and a plurality of straight lines radially stretching from a center of the concentric circles as radiation rays, and the plurality of concentric circles and the plurality of straight lines differ in their widths and said detecting part detects a part of the pattern.

25. An ultrasonic low attenuation medium according to claim 18, wherein
said prescribed pattern includes a plurality of concentric circles and a plurality of straight lines radially stretching from a center of the concentric circles as radiation rays, and the plurality of concentric circles and the plurality of straight lines differ in their widths.

* * * * *